United States Patent [19]

Phillipson et al.

[11] Patent Number: 5,077,277

[45] Date of Patent: Dec. 31, 1991

[54] CHEMICAL DERIVATIVES OF ANTIBIOTICS LL-E19020 ALPHA AND BETA

[75] Inventors: Douglas W. Phillipson, Princeton, N.J.; Guy T. Carter; Donald B. Borders, both of Suffern, N.Y.

[73] Assignee: American Cyanamid Company, Wayne, N.J.

[21] Appl. No.: 403,232

[22] Filed: Sep. 5, 1989

[51] Int. Cl.$^5$ .................. A61K 31/70; C07H 7/00
[52] U.S. Cl. .................................. 514/25; 514/23; 536/16.8; 536/17.9; 536/18.7; 536/53; 536/55
[58] Field of Search ............... 536/115, 16.8, 17.9, 536/18.7, 53, 55; 514/23, 25

[56] References Cited

U.S. PATENT DOCUMENTS

| | | | |
|---|---|---|---|
| 4,704,276 | 11/1987 | Kantor | 424/122 |
| 4,705,680 | 11/1987 | Vellkoop | 424/55 |
| 4,705,688 | 11/1987 | Carter et al. | 424/122 |
| 4,753,798 | 6/1988 | Kantor et al. | 424/122 |

*Primary Examiner*—Elli Peselev
*Attorney, Agent, or Firm*—Kenneth J. Dow

[57] ABSTRACT

Derivatives of antibiotics derived from the microorganism *Streptomyces lydicus* subspecies tanzanius, referred to as antibiotics LL-E19020 alpha and beta, are produced by chemical reaction. The derivatives are also active antibiotics useful in the treatment of bacterial infections.

7 Claims, 21 Drawing Sheets

CHEMICAL DERIVATIVES OF ANTIBIOTICS LL-E19020 ALPHA AND BETA

BACKGROUND OF THE INVENTION

This invention relates to novel antibacterial compounds and to the treatment of bacterial infections in animals in need of such treatment. The antibiotics LL-E19020 α and β are disclosed and claimed by physical/chemical characteristics in U.S. Pat. No. 4,705,688, the contents of which are hereby incorporated by reference. These antibiotics, derived from the microorganism *streptomyces lydicus* subspecies tanzanius NRRL 18036, are active as antibacterial agents. They are also growth promoters, anti-protozoan agents, and anthelmintic agents.

Another complex of antibiotics named Phenelfamycins has been disclosed by Abbott Laboratories, Abbott Park, Ill. at the 27th Interscience Conference on Antimicrobial Agents and Chemotherapy, New York, NY in October, 1987.

The structures of LL-E19020 α and β are reproduced below:

and LL-E19020 β which also have activity as antibacterial agents.

SUMMARY OF THE INVENTION

Accordingly, this invention is concerned with chemically prepared derivatives of LL-E19020 α and β which are also antimicrobial agents and which are described below by their structures and physical/-chemical characteristics together with methods for their preparation.

Because Chemical Abstract names have not as yet been assigned to these structures, they will be referred to as derivatives of LL-E19020 α and β throughout the balance of this text.

Ammonolysis Product of LL-E19020 α and β

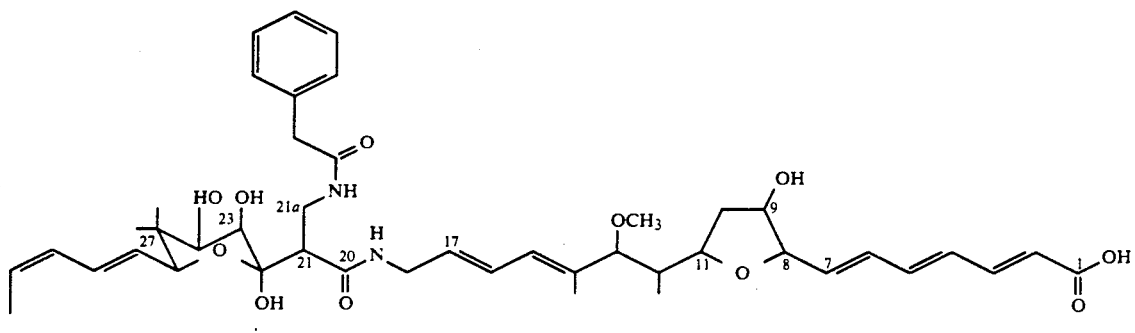

The ammonolysis product of LL-E19020 α and β has ultraviolet absorption spectra as shown in FIG. I; an infrared absorption spectrum as shown in FIG. II; a proton magnetic resonance spectrum as shown in FIG. III; and a carbon-13-nuclear magnetic resonance spectrum as shown in FIG. IV.

The ammonolysis product of LL-E19020 α and β is prepared by dissolving LL-E19020 α or β in acetonitrile, reacting with ammonium hydroxide for 12-24

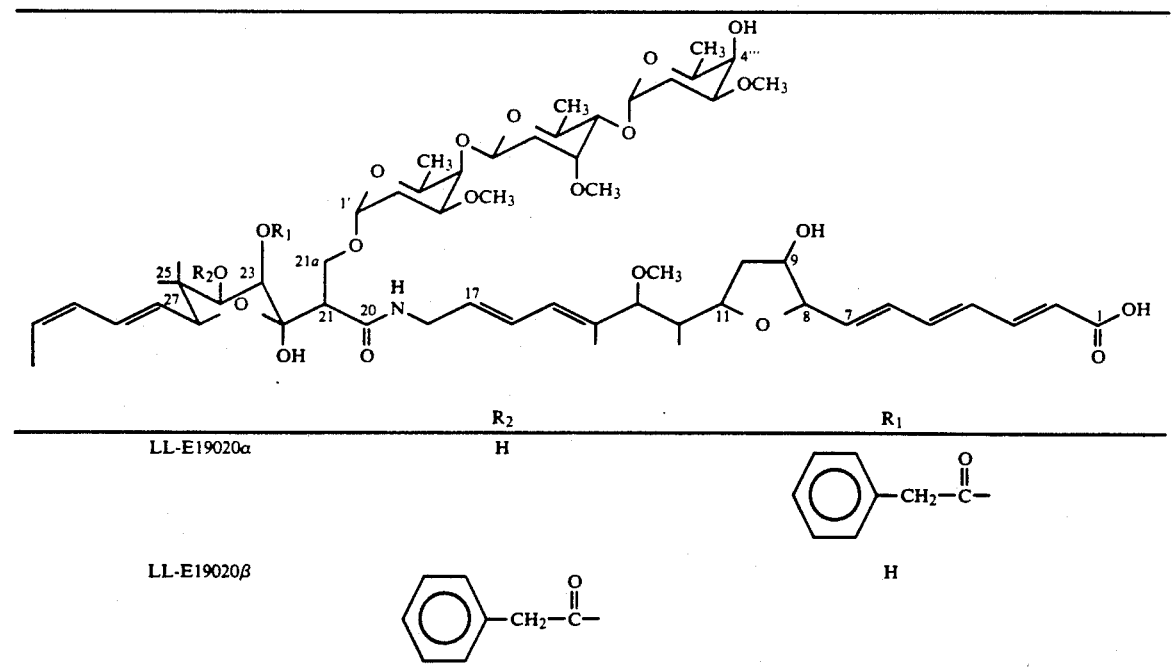

An object of the present invention is to provide chemical derivatives of the antibiotics LL-E19020 α hours, diluting with water and acidifying with hydrochloric acid to pH 1. This solution is extracted into ethyl acetate, evaporated and then purified by chromatography.

Methyl Esters of LL-E19020α and β

The monosaccharide of the methyl ester of LL-E19020α has an infrared spectrum as shown in FIG. VI; a proton magnetic resonance spectrum as shown in FIG. VII; and a carbon-13-magnetic resonance spectrum as shown in FIG. VIII.

The monosaccharide of the methyl esters of LL-

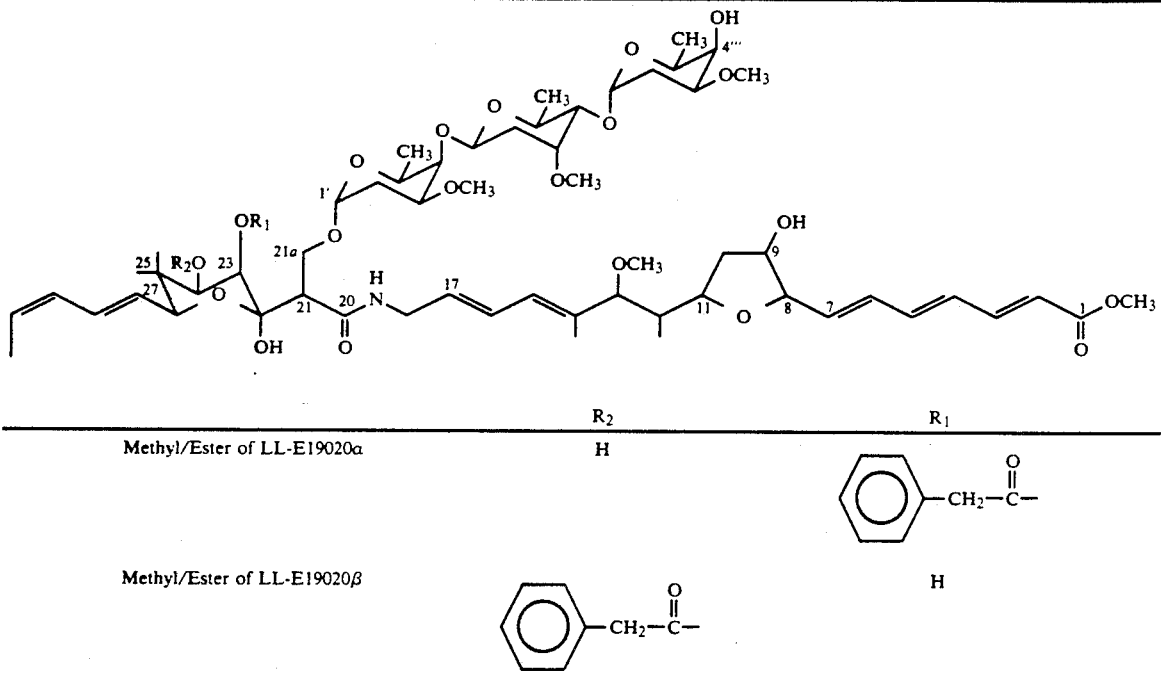

The methyl ester of LL-E19020β has a proton magnetic resonance spectrum as shown in FIG. V.

The methyl esters of LL-E9020 α and β are prepared by dissolving either LL-E19020 α or β in a solvent such as ethyl acetate, acetonitrile or dichloromethane, or mixtures thereof, followed by reaction with ethereal diazomethane and purification by chromatography.

Monosaccharides of the Methyl Esters of LL-E19020 α and β

E19020 α and β are prepared by dissolving the methyl ester of LL-E19020 α or β in methanol, cooling to 0° C. and reacting with dilute hydrochloric acid in methanol for several hours, followed by dilution with water, extraction into ethyl acetate and purification by chromatography.

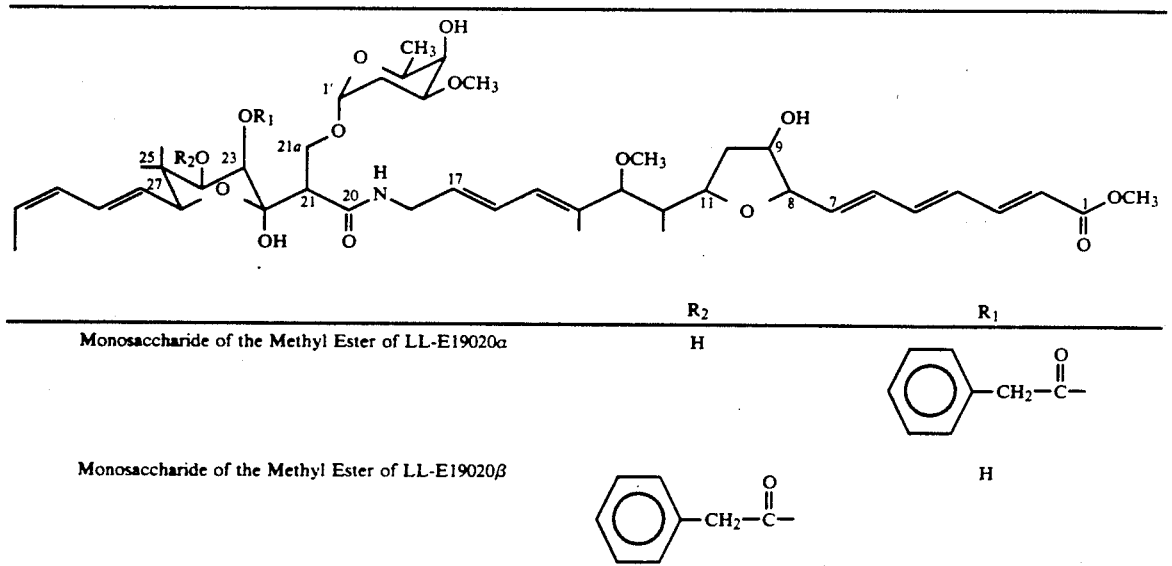

Aglycone of the Methyl Esters of LL-E19020 α and β

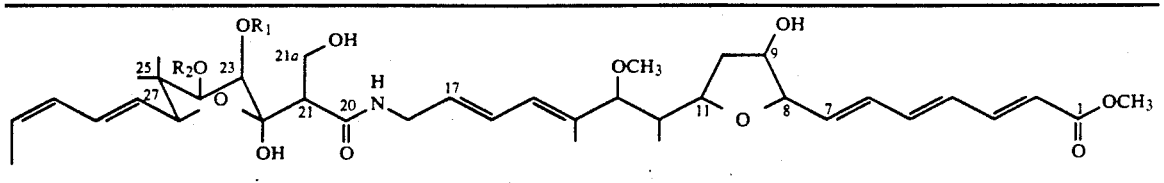

| | $R_2$ | $R_1$ |
|---|---|---|
| Aglycone of the Methyl Ester of LL-E19020α | H | 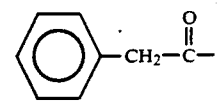 |
| Aglycone of the Methyl Ester of LL-E19020β | 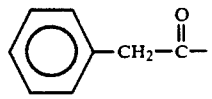 | H |

The aglycone of the methyl ester of LL-E19020α has ultraviolet absorption spectra as shown in FIG. IX; an infrared absorption spectrum as shown in FIG. X; a proton magnetic resonance spectrum as shown in FIG. XI; and a carbon-13-nuclear magnetic resonance spectrum as shown in FIG. XII.

The aglycone of the methyl ester of LL-E19020β has ultraviolet absorption spectra as shown in FIG. XIII; an infrared absorption spectrum as shown in FIG. XIV; a proton magnetic resonance spectrum as shown in FIG. XV; and a carbon-13-magnetic resonance spectrum as shown in FIG. XVI.

The aglycone of the methyl esters of LL-E19020 α and β are prepared by reacting the methyl ester of LL-E19020 α or β with hydrochloric acid in methanol at reduced temperature for several hours, followed by extraction into ethyl acetate and chromatographic purification.

Triacetate of the Aglycone Methyl Ester of LL-E19020 α and β shown in FIG. XVIII; and a carbon-13-nuclear magnetic resonance spectrum as shown in FIG. XIX.

The triacetate of the aglycone methyl ester of LL-E19020β has a proton magnetic resonance spectrum as shown in FIG. XX; and a carbon-13-nuclear magnetic resonance spectrum as shown in FIG. XXI.

The triacetate of the aglycone methyl ester of LL-E19020 α and β is prepared by reacting the aglycone methyl ester of LL-E19020 α or β with a solution of 4-dimethylamino pyridine and acetic anhydride in dichloromethane for several hours followed by purification by chromatography.

DESCRIPTION OF THE DRAWINGS

The above noted and other features of the invention will be best understood from the following detailed description, when considered with reference to the accompanying drawings mentioned above, in which:

FIG. I is an ultraviolet absorption spectrum of the ammonolysis product in acidic, basic and alcoholic solutions;

Figure 1:
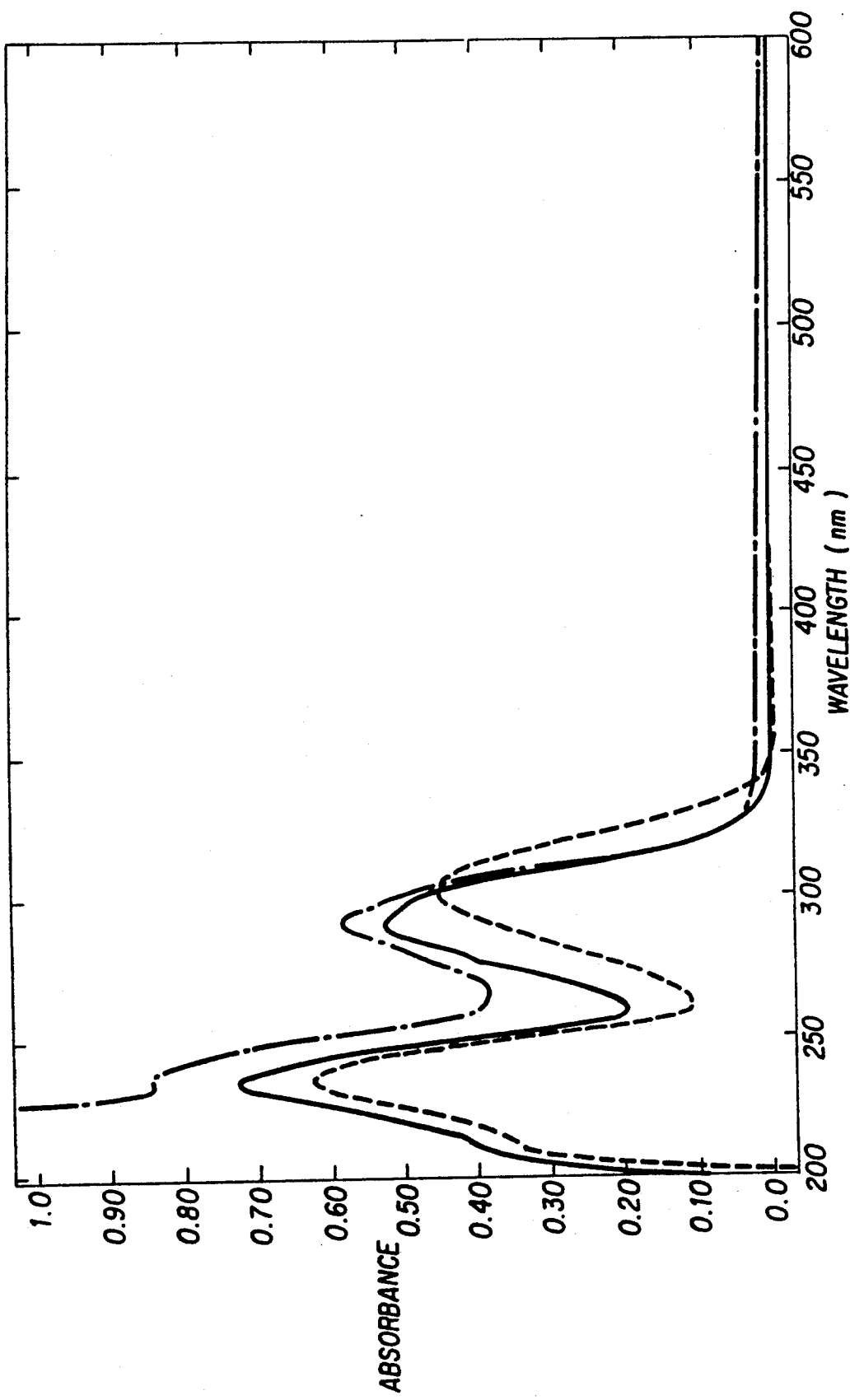
Figure 2:
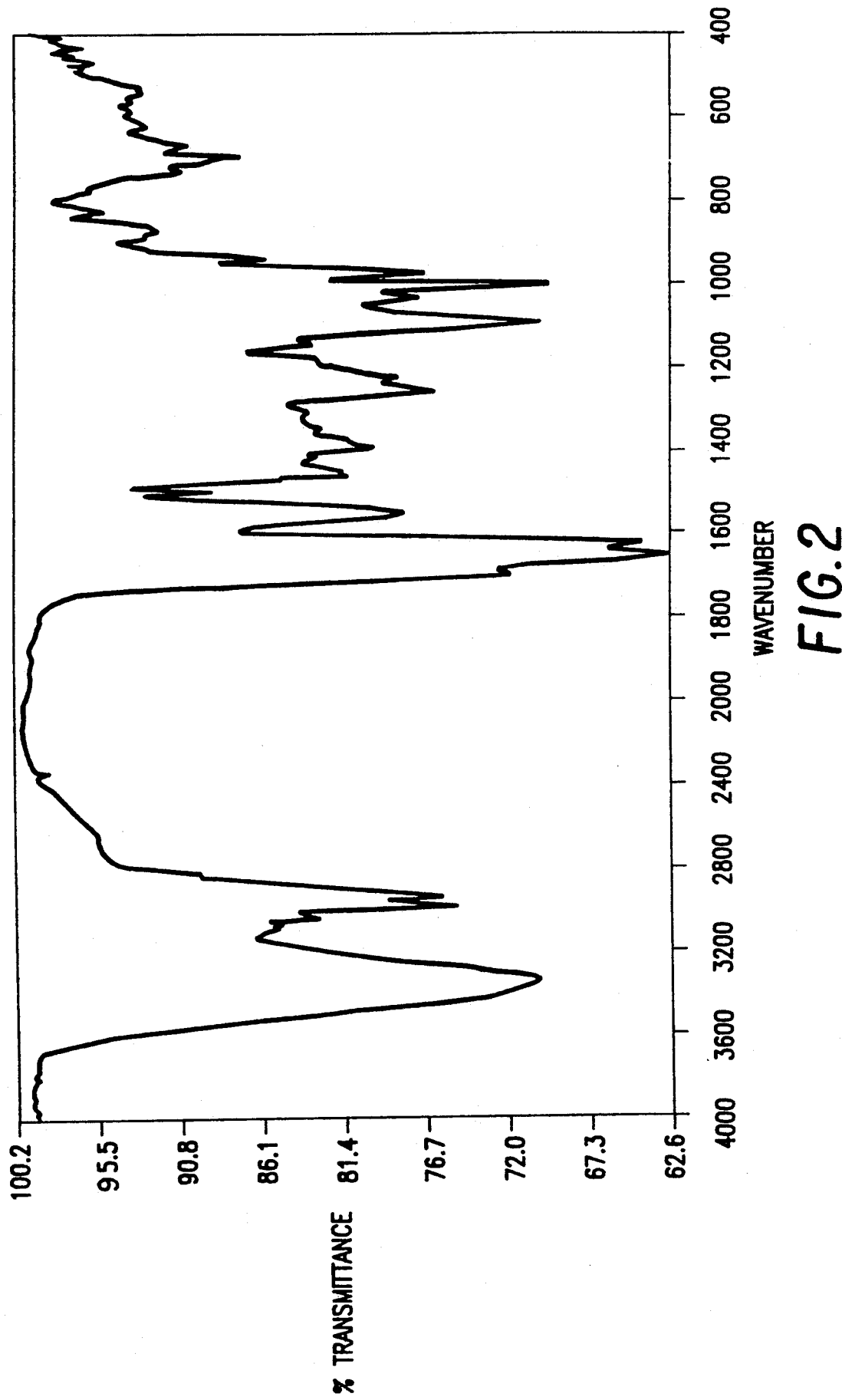
Figure 3:
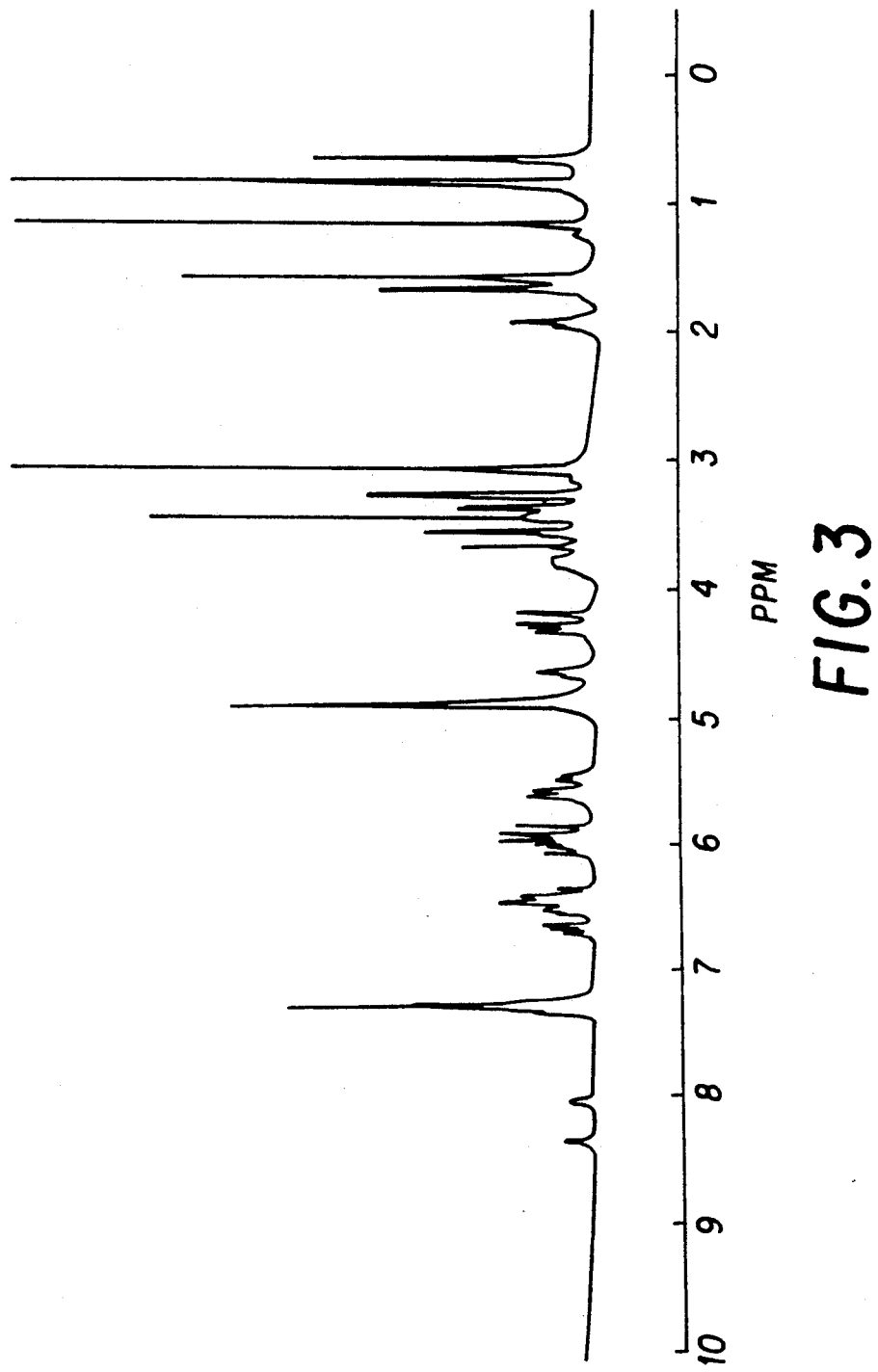
Figure 4:
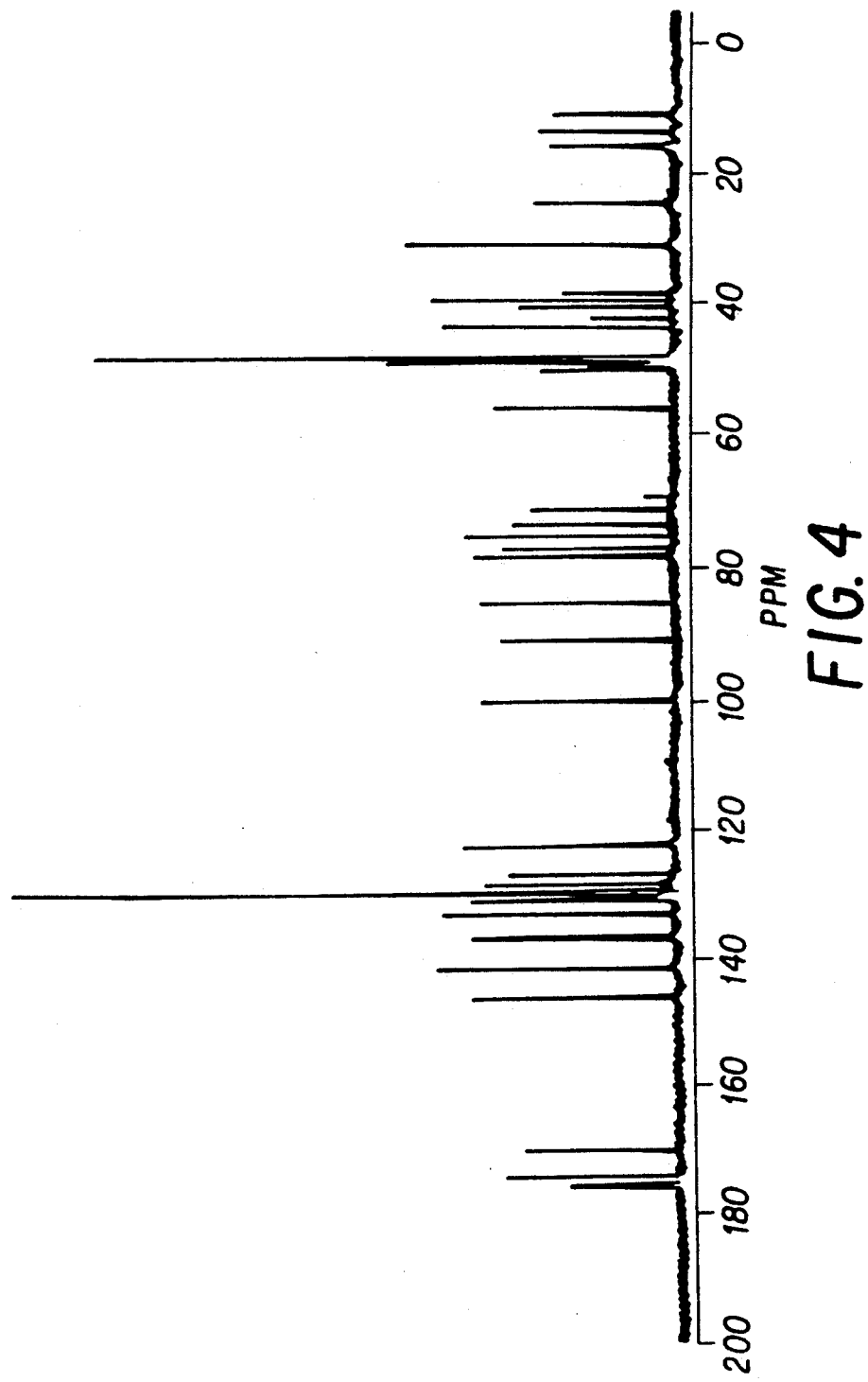
Figure 5:
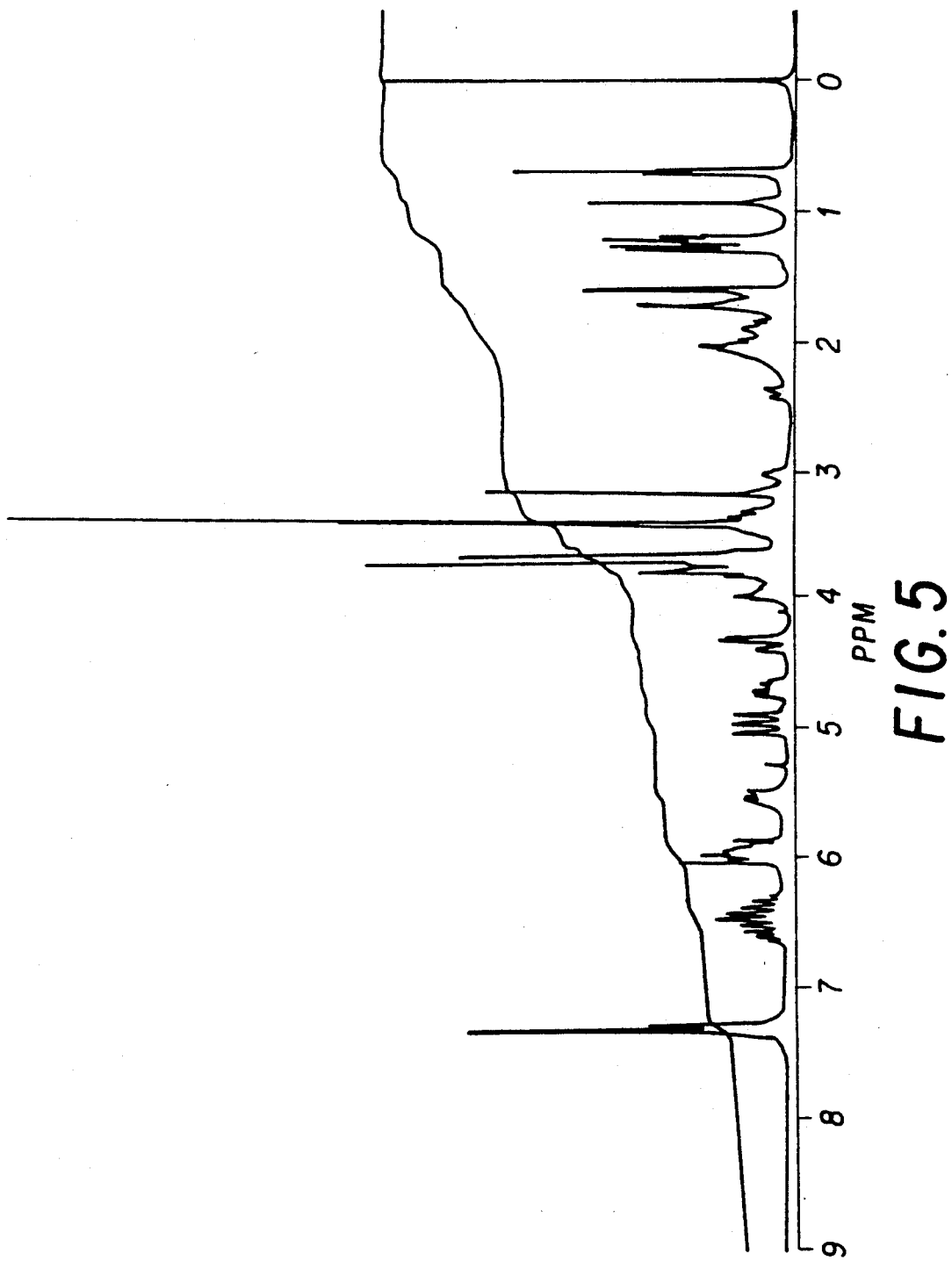
Figure 6:
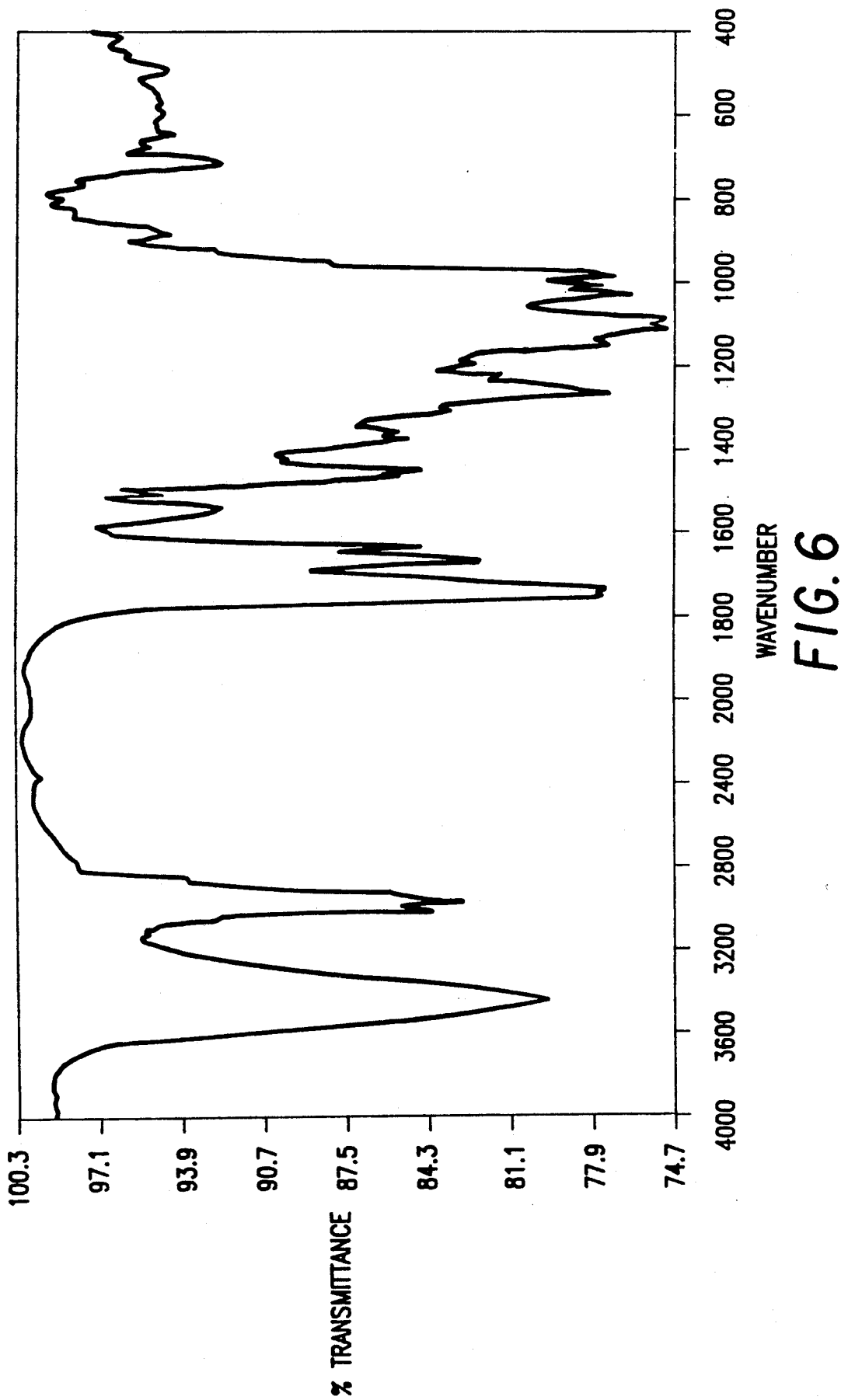
Figure 7:
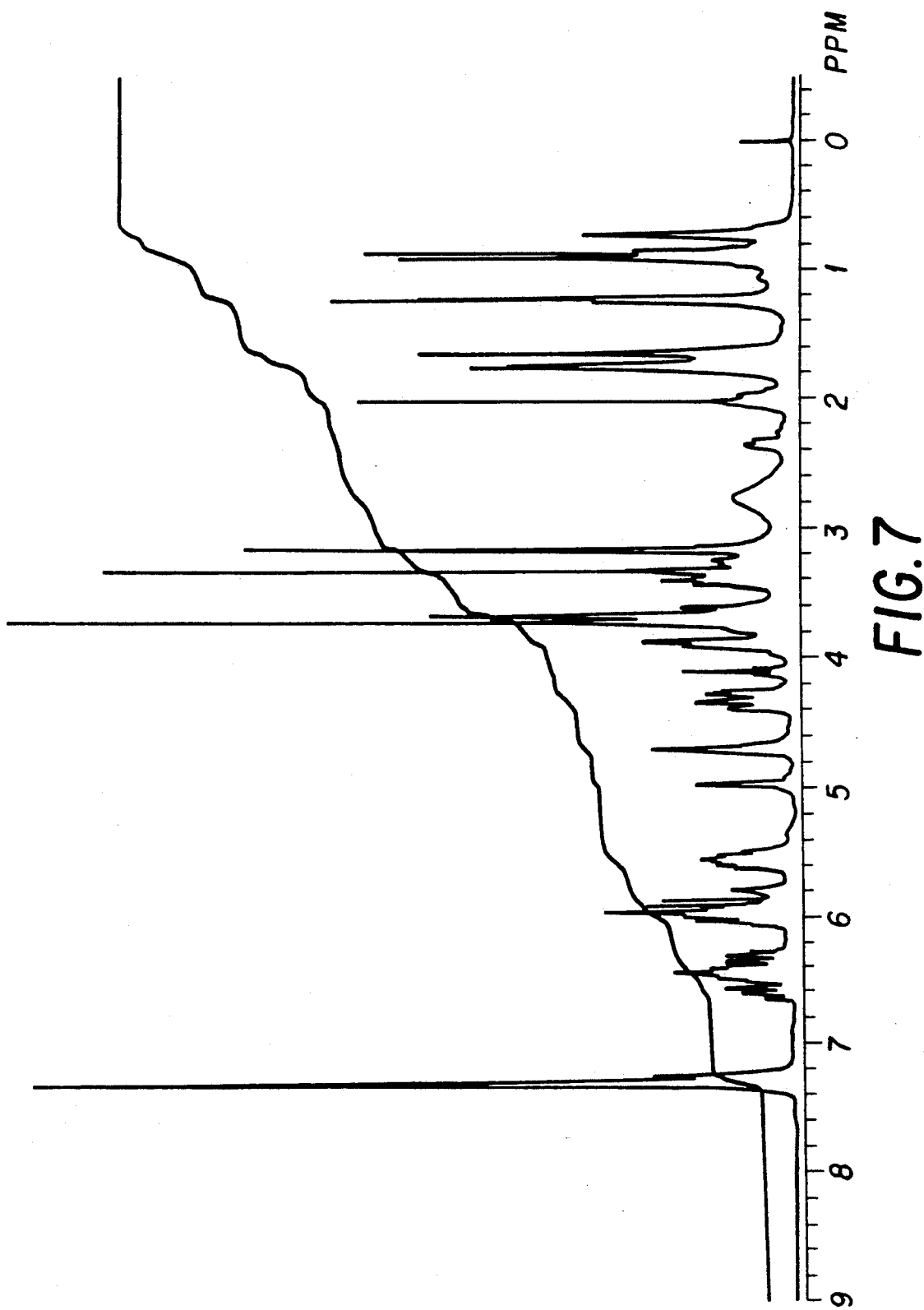
Figure 8:
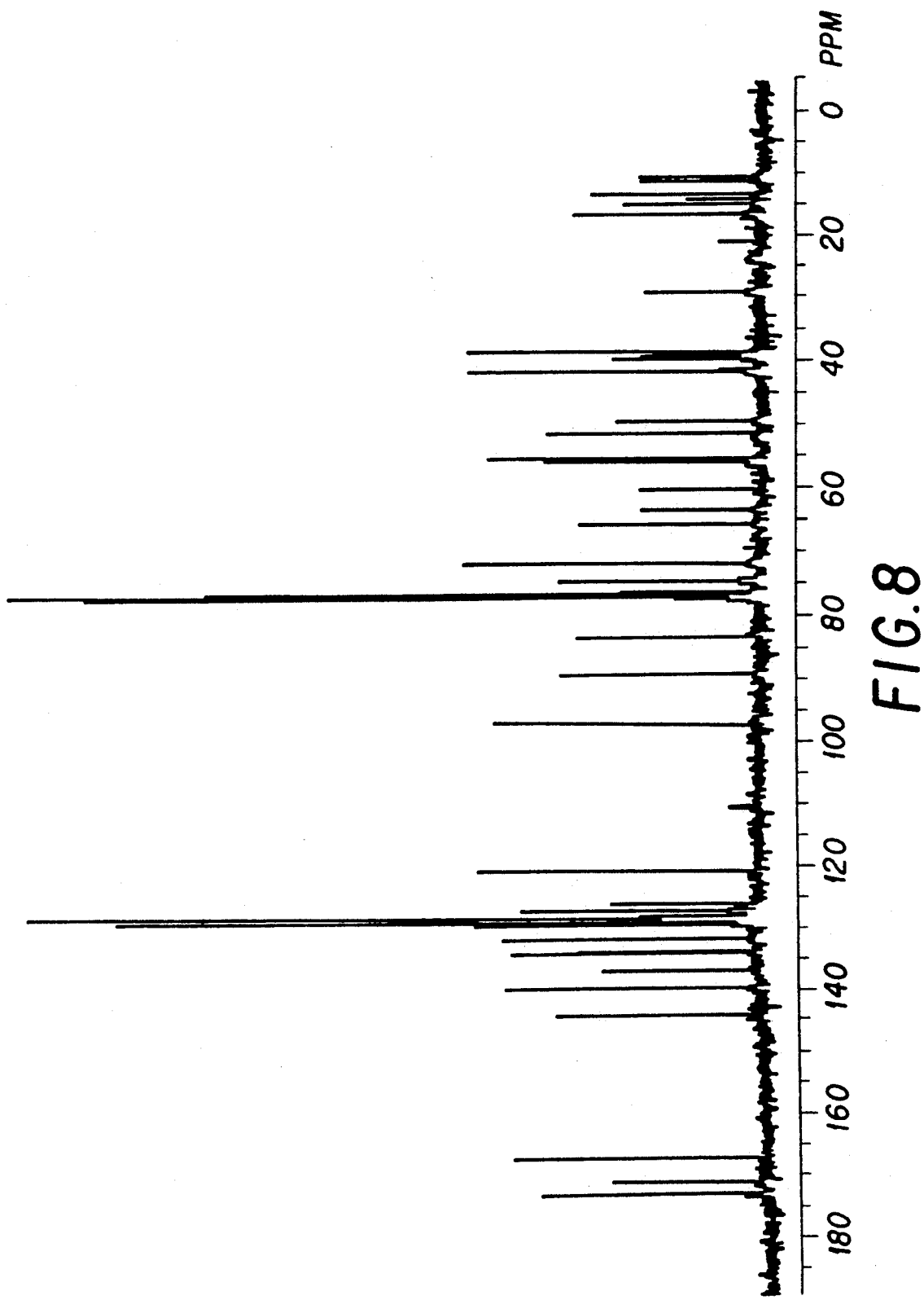
Figure 9:
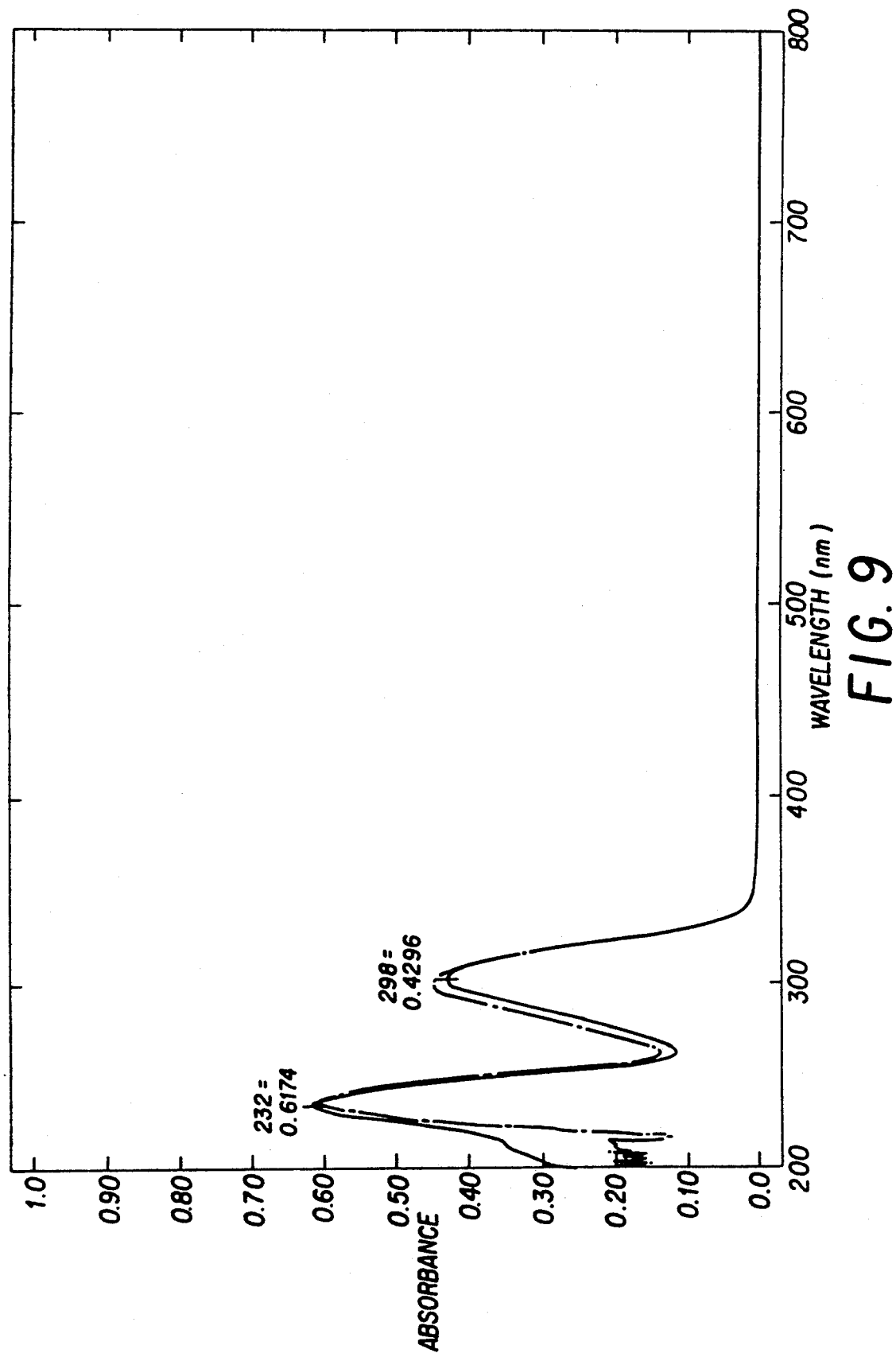
Figure 10:
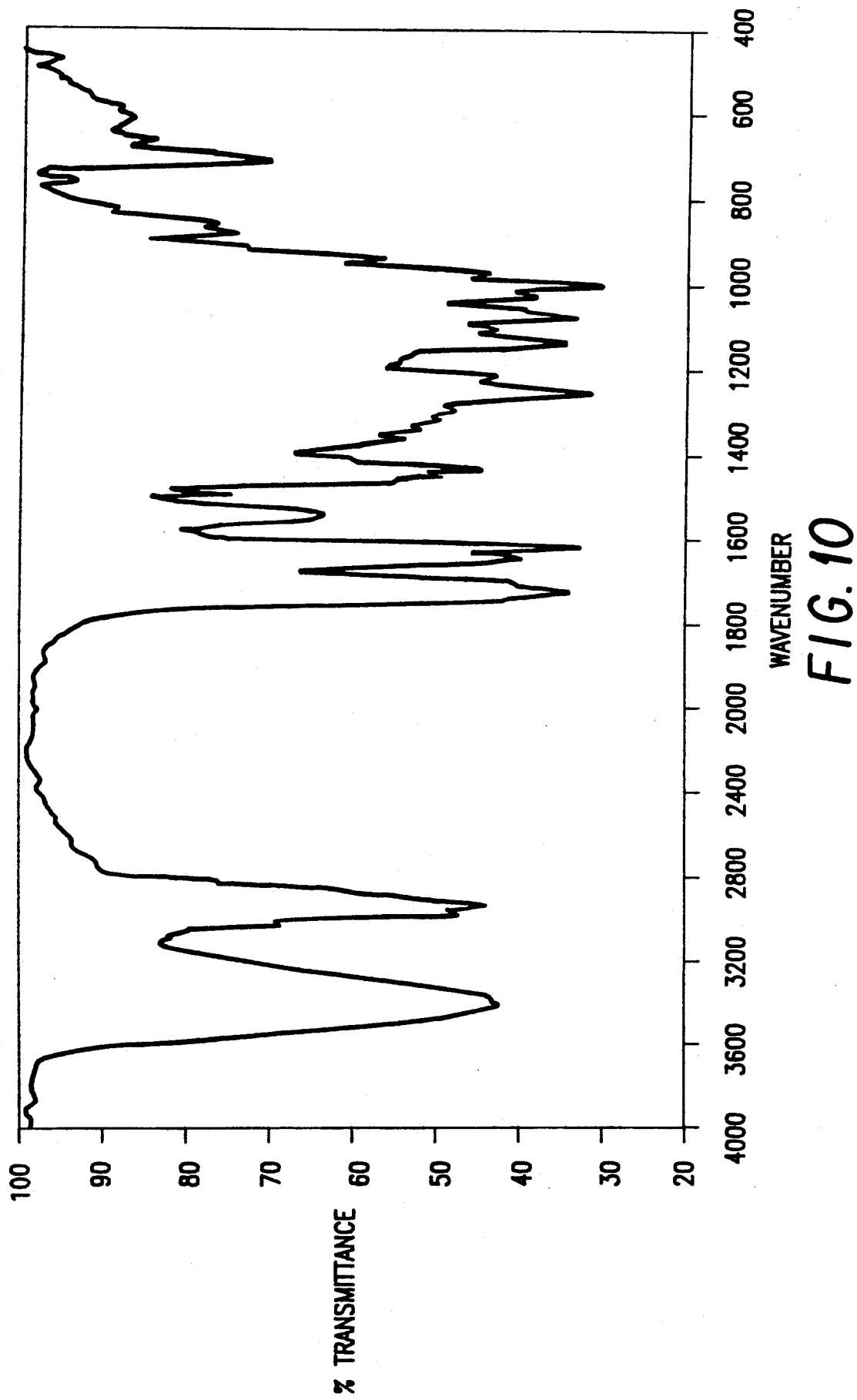
Figure 11:
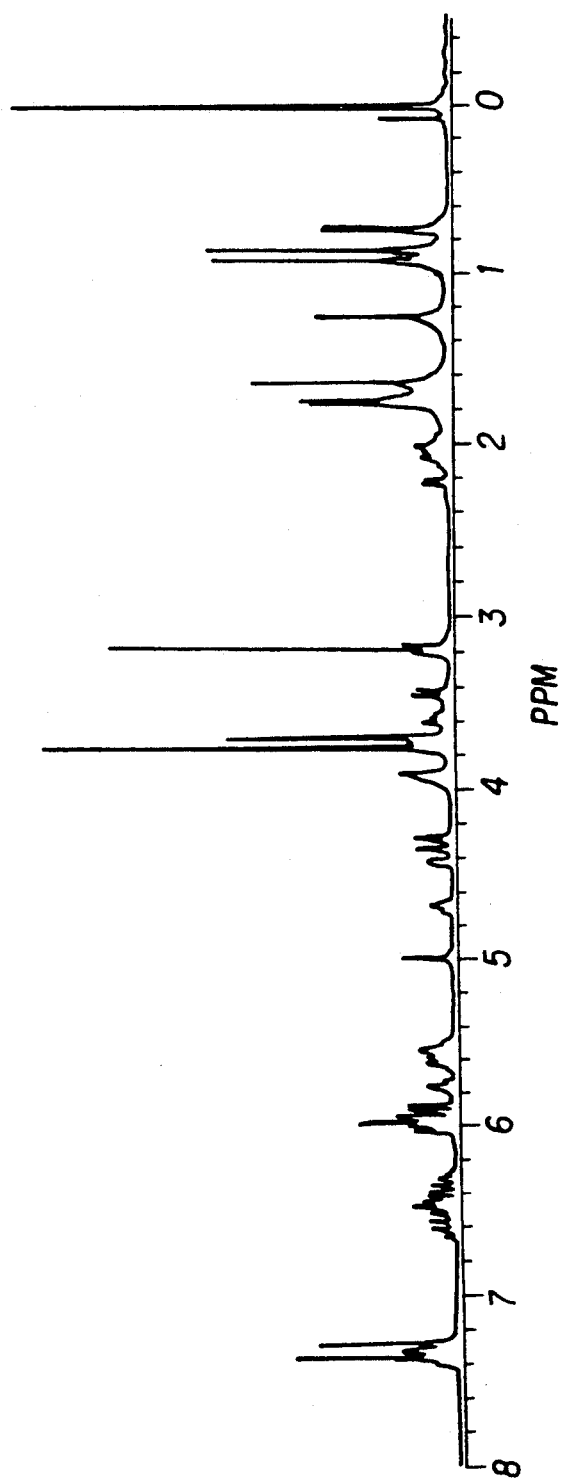
Figure 12:
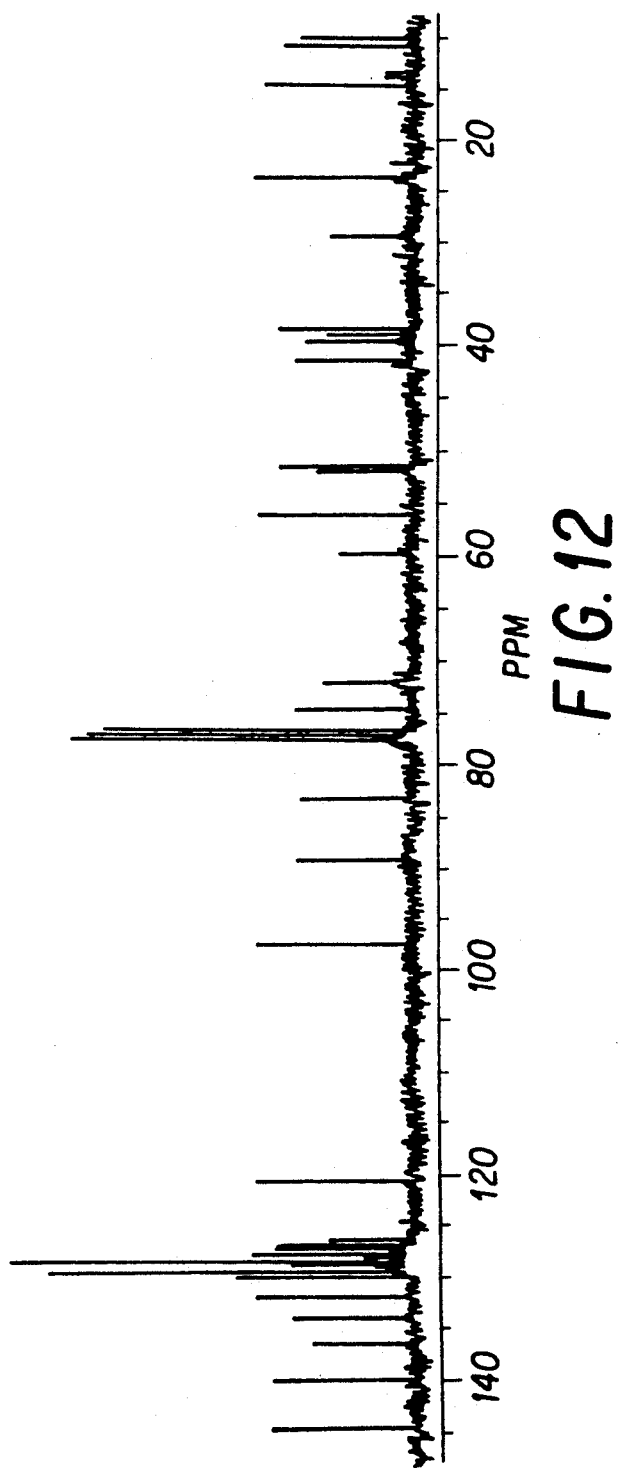
Figure 13:
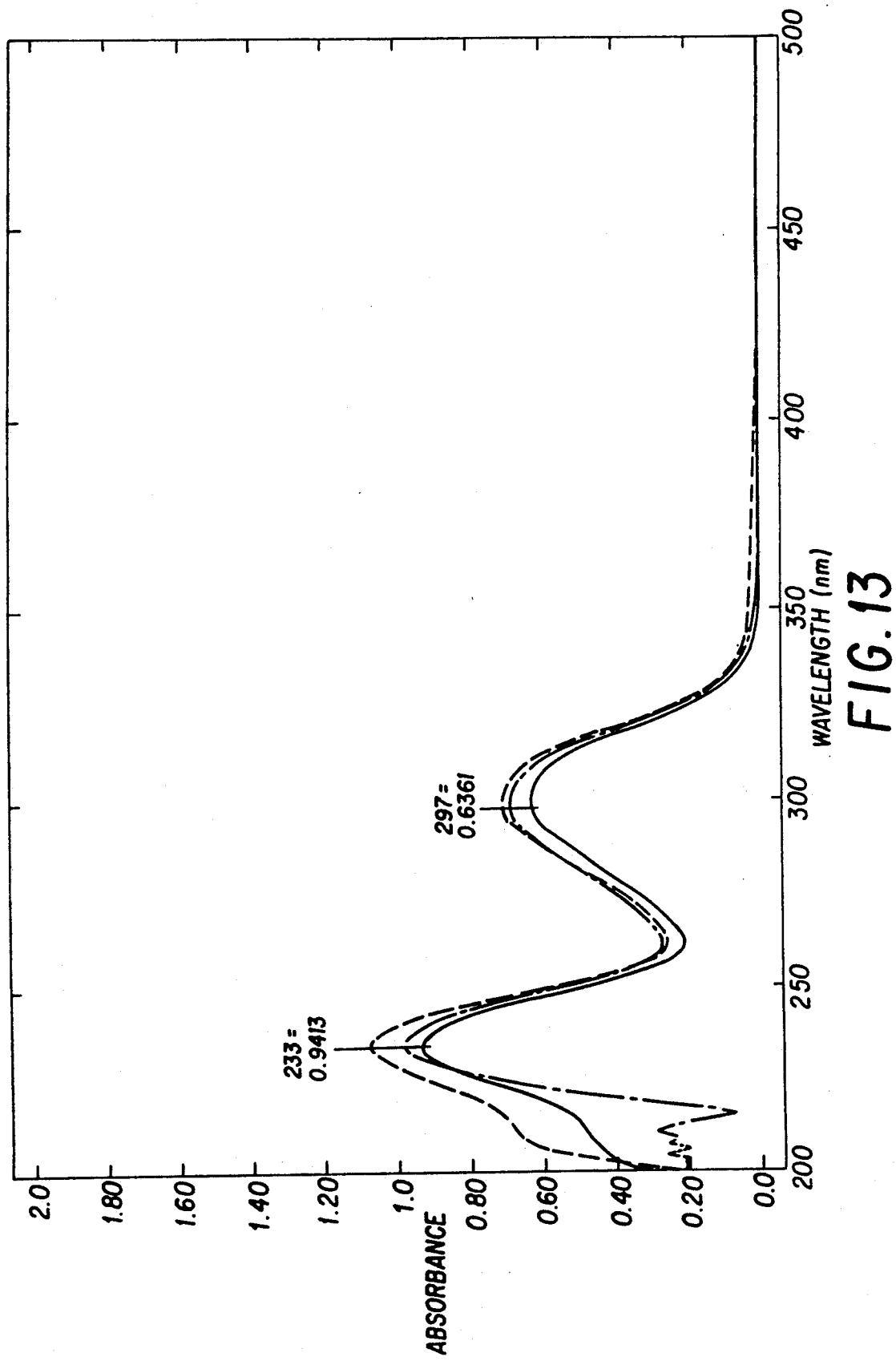
Figure 14:
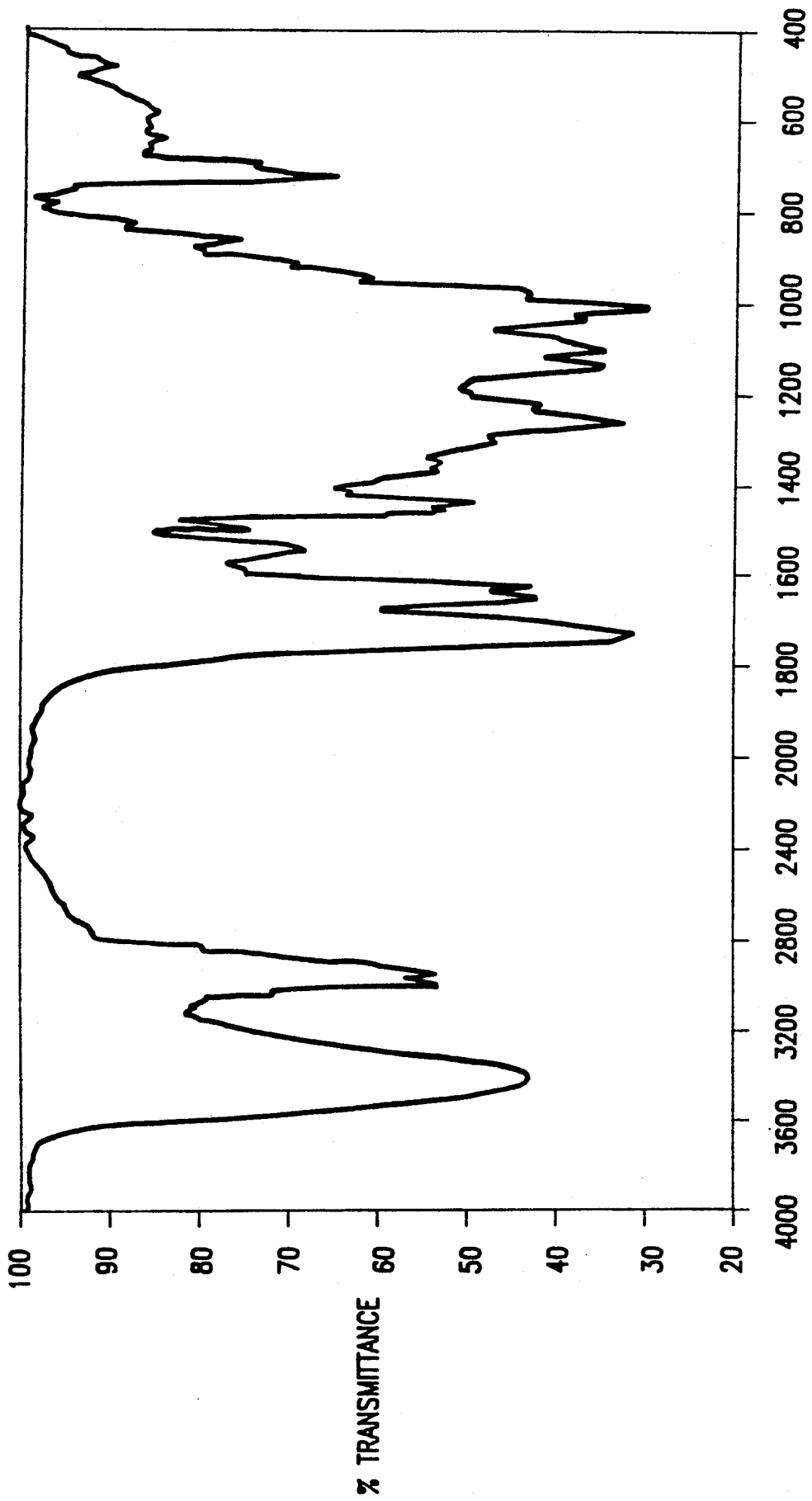
Figure 15:
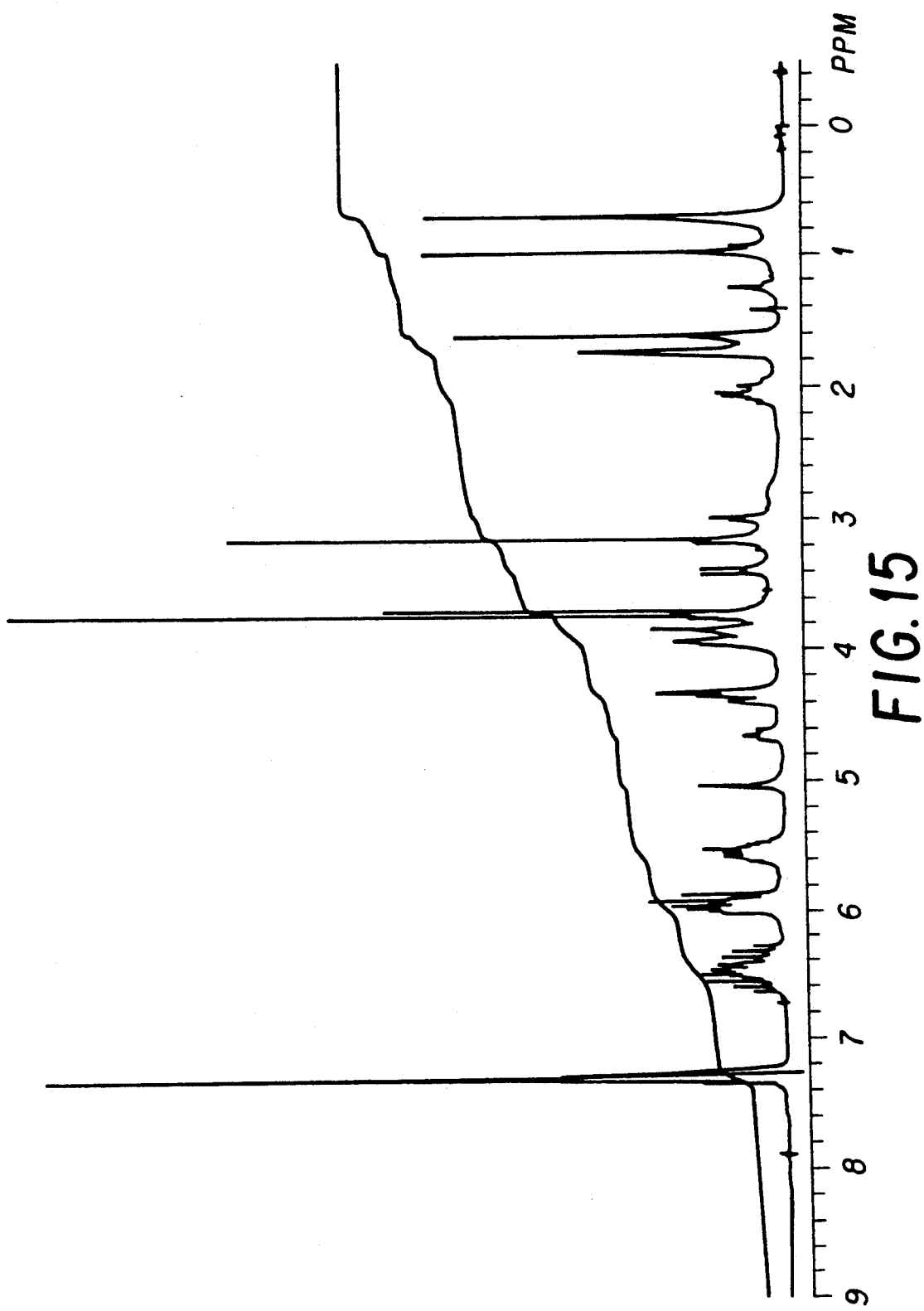
Figure 16:
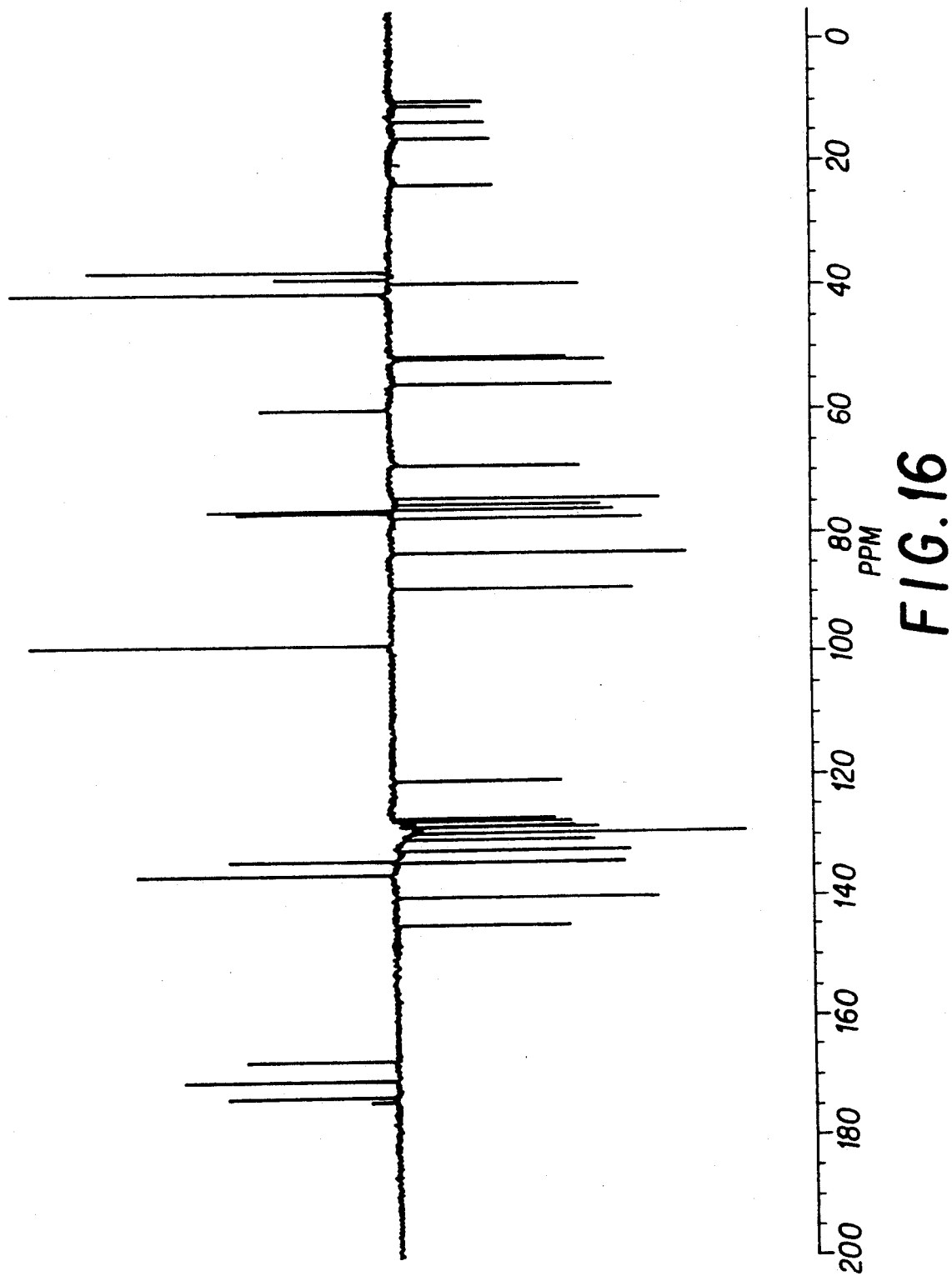
Figure 17:
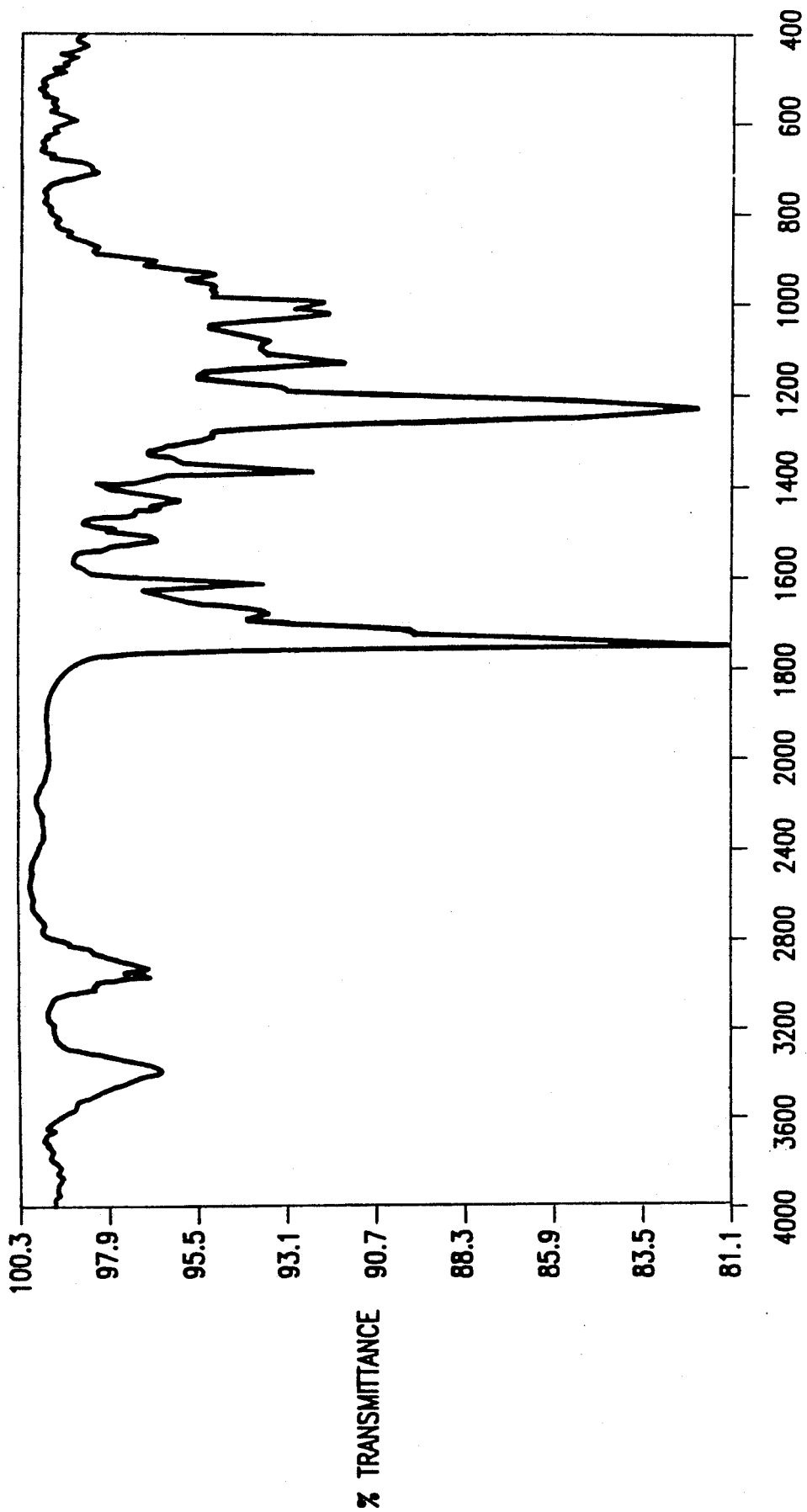
Figure 18:
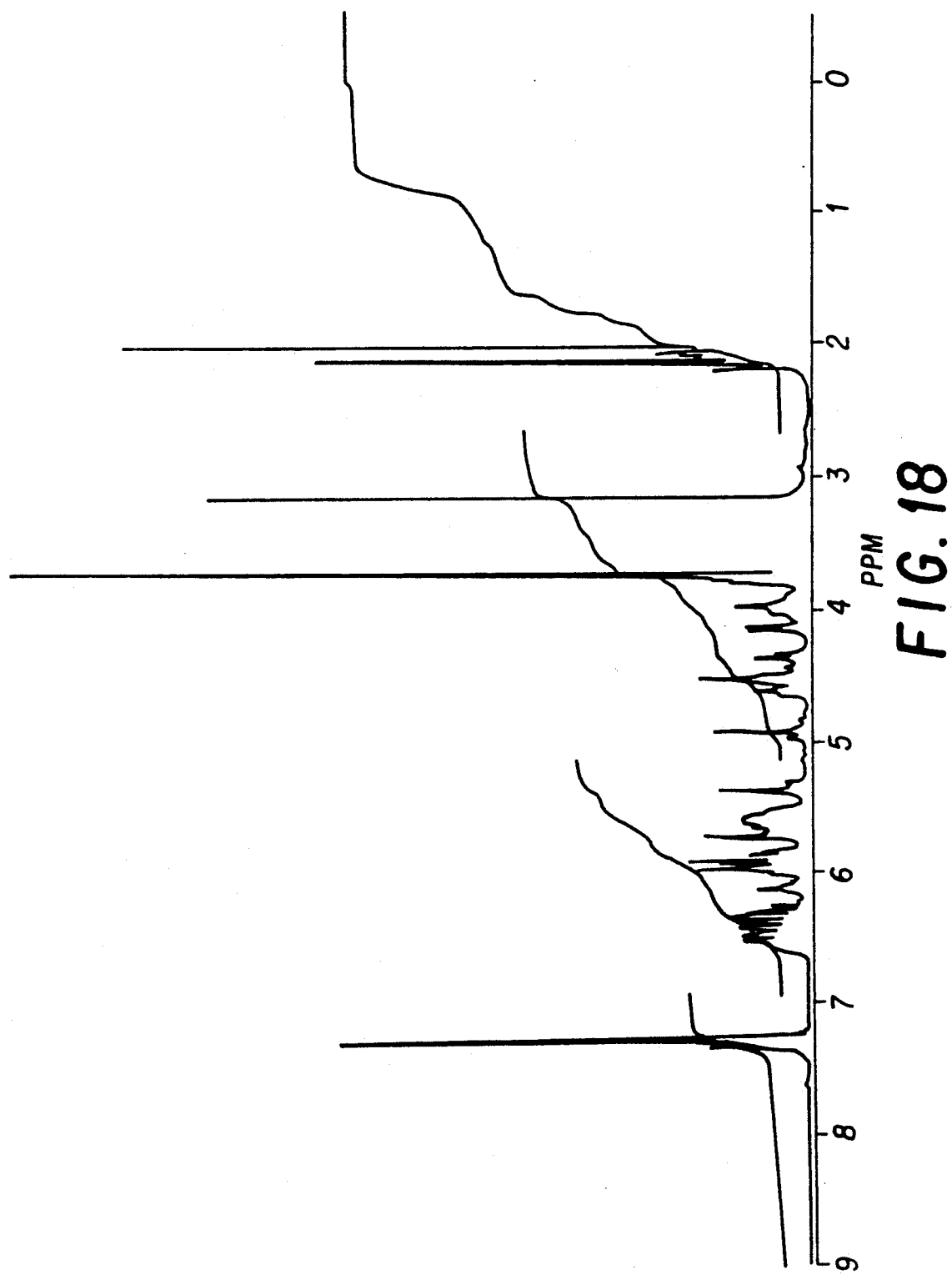
Figure 19:
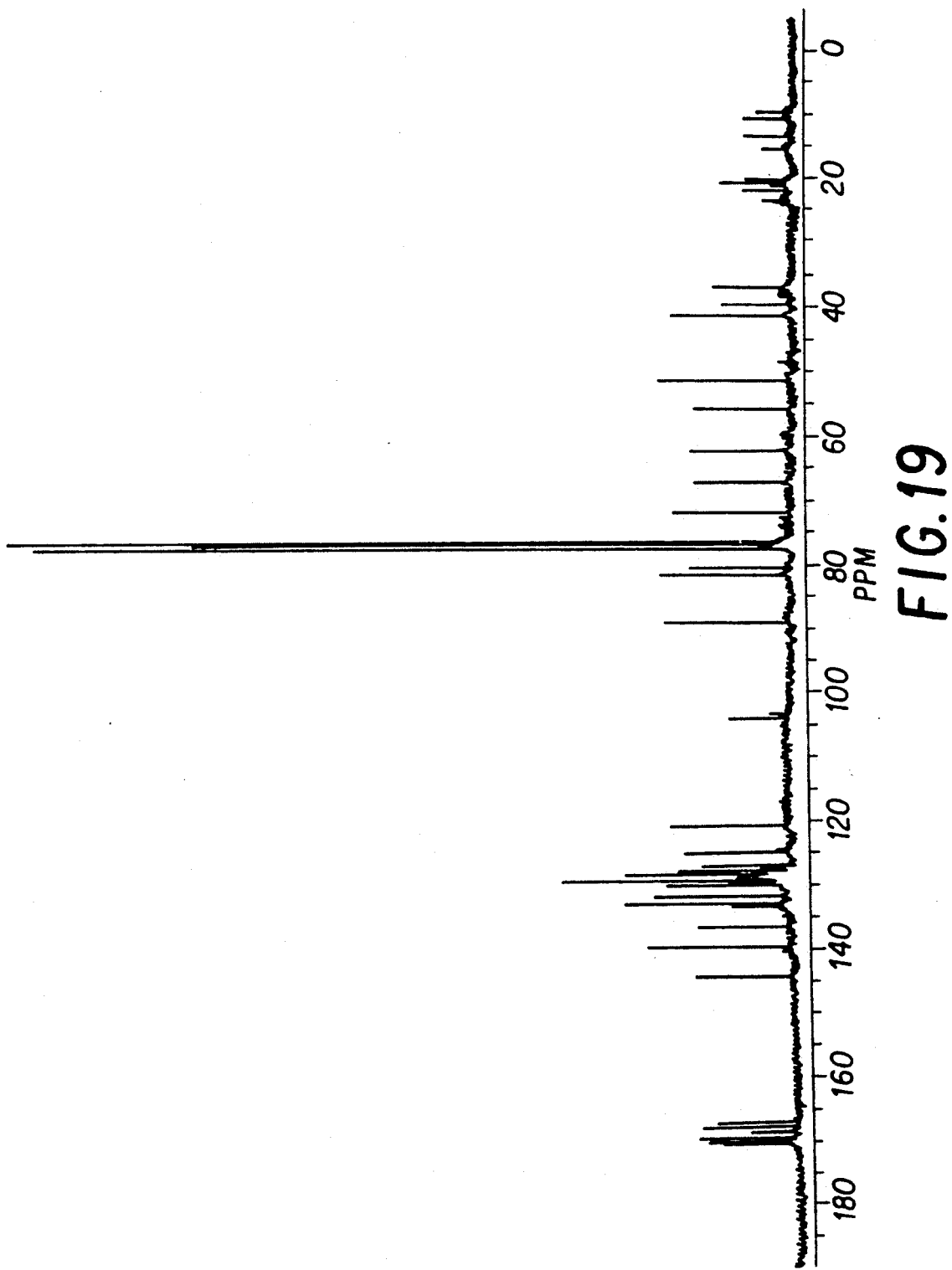
Figure 20:
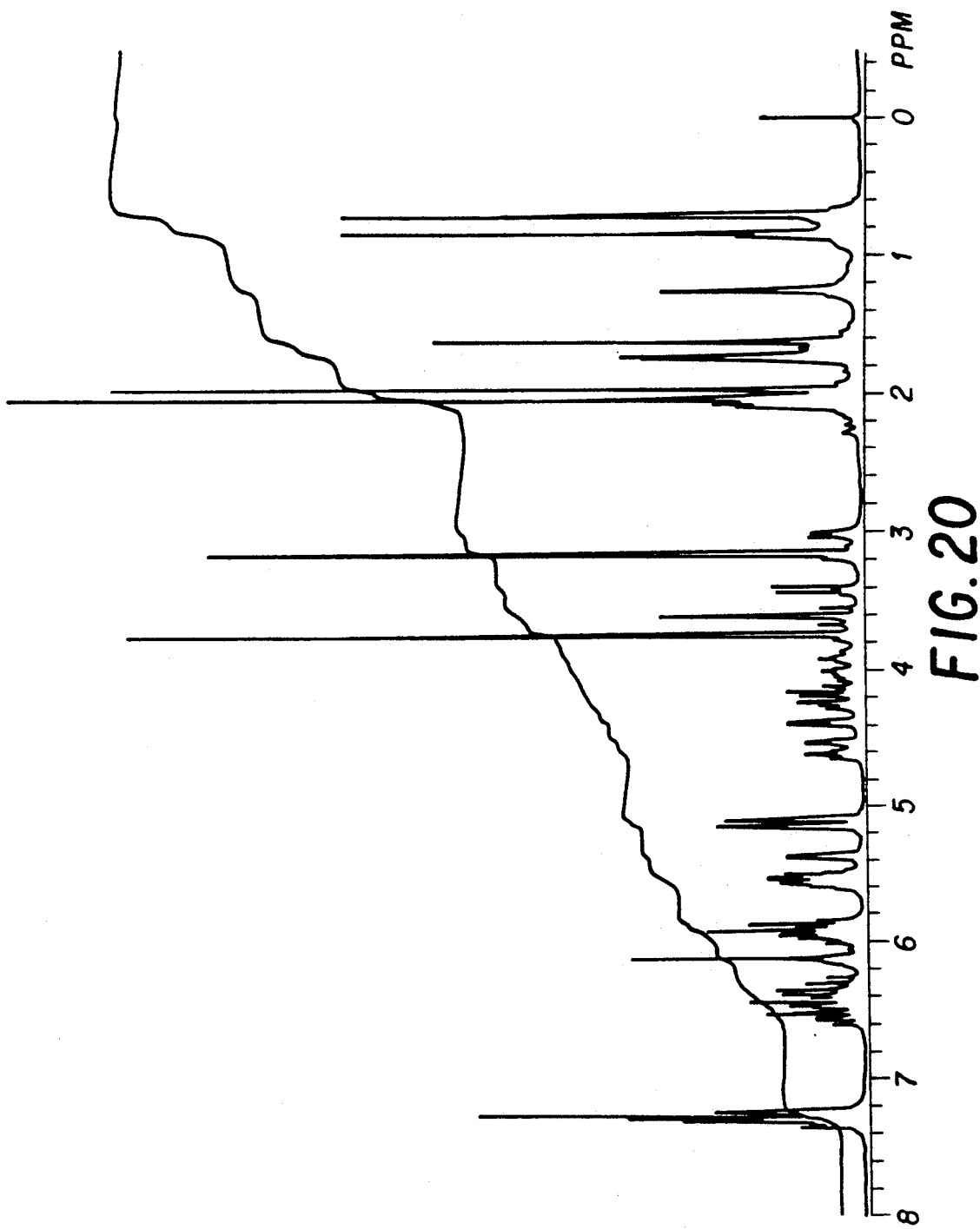
Figure 21:
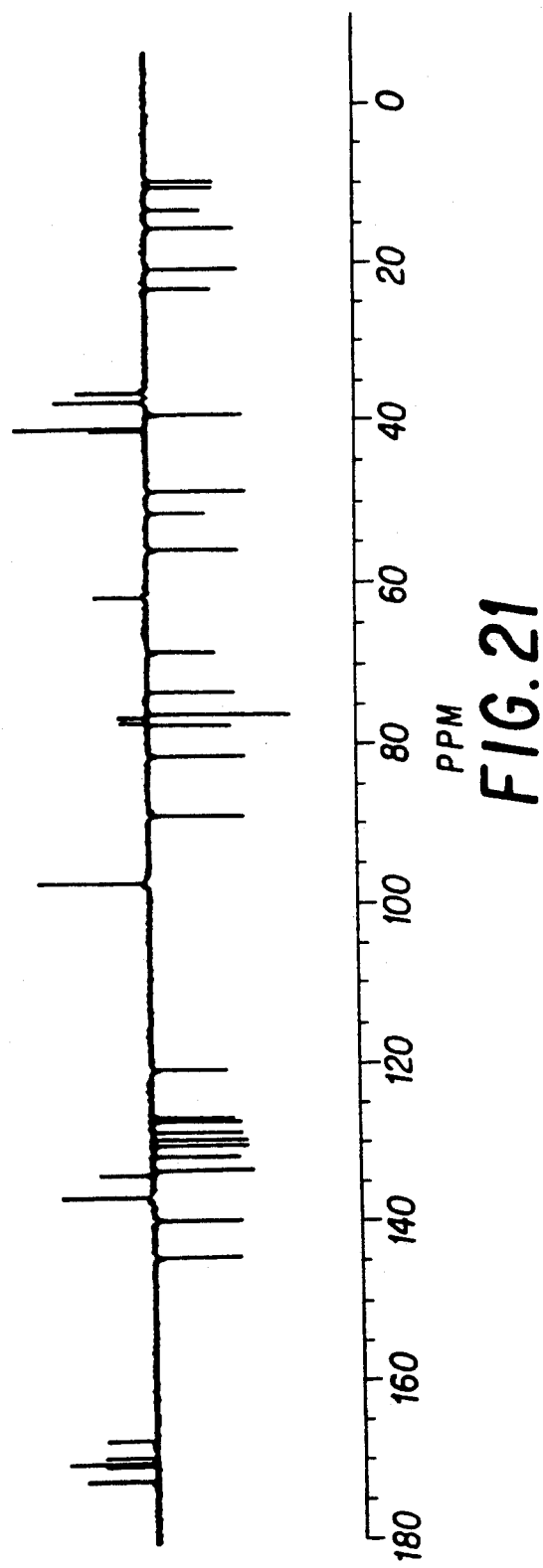

FIG. II is an infrared absorption spectrum of the ammonolysis product of LL-E19020β dispersed in po-

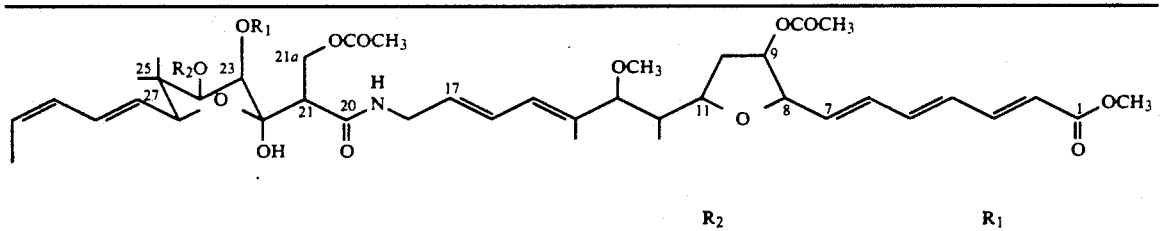

| | $R_2$ | $R_1$ |
|---|---|---|
| Triacetate of the Aglycone Methyl Ester of LL-E19020α |  | 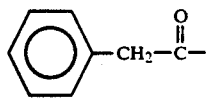 |
| Triacetate of the Aglycone Methyl Ester of LL-E19020β | 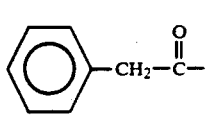 | 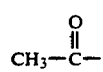 |

The triacetate of the aglycone methyl ester of LL-E19020α has an infrared absorption spectrum as shown in FIG. XVII; a proton magnetic resonance spectrum as tassium bromide;

FIG. III is a proton magnetic resonance spectrum of the ammonolysis product;

FIG. IV is a carbon-13-nuclear magnetic resonance print-out of the ammonolysis product of LL-E19020β;

FIG. V is a proton magnetic resonance spectrum of the methyl ester of LL-E19020β;

FIG. VI is an infrared absorption spectrum of the monosaccharide of the methyl ester of LL-E19020α dispersed in potassium bromide;

FIG. VII is a print-out of the proton magnetic spectrum of the monosaccharide of the methyl ester of LL-E19020α;

FIG. VIII is a print-out of the carbon-13-magnetic resonance spectrum of the monosacchoride of the methyl ester of LL-E19020α;

FIG. IX is an ultraviolet absorption spectrum of the aglycone of the methyl ester of LL-E19020α;

FIG. X is an infrared absorption spectrum of the aglycone of the methyl ester of LL-E19020α in potassium bromide;

FIG. XI is a proton magnetic resonance spectrum print-out of the aglycone of the methyl ester of LL-E19020α;

FIG. XII is a carbon-13-nuclear magnetic resonance spectrum of the aglycone of the methyl ester of LL-E19020α;

FIG. XIII is the ultraviolet absorption spectrum of the aglycone of the methyl ester of LL-E19020β;

FIG. XIV is the infrared absorption spectrum of the aglycone of the methyl ester of LL-E19020β in potassium bromide;

FIG. XV is the proton magnetic resonance spectrum of the aglycone of the methyl ester of LL-E19020β;

FIG. XVI is the carbon-13-nuclear magnetic resonance spectrum of the aglycone of the methyl ester of LL-E19020β;

FIG. XVII is the infrared absorption spectrum of the triacetate of the aglycone methyl ester of LL-E19020α in potassium bromide;

FIG. XVIII is the proton magnetic resonance spectrum of the triacetate of the aglycone methyl ester of LL-E19020α;

FIG. XIX is the carbon-13-nuclear magnetic resonance spectrum of the triacetate of the aglycone methyl ester of LL-E19020α;

FIG. XX is the proton magnetic resonance spectrum of the triacetate of the aglycone methyl ester of LL-E19020β;

FIG. XXI is the carbon-13-nuclear magnetic resonance spectrum of the triacetate of the aglycone methyl ester of LL-E19020β.

DESCRIPTION OF THE INVENTION

The in vitro antibacterial activity of these compounds was determined against a spectrum of gram-positive and gram-negative bacteria and anaerobes by a standard agar dilution method. Mueller-Hinton agar containing 5% sheep blood or Wilkins Chalgren agar and two-fold decreasing concentrations of the test compounds were poured into petri dishes. The agar surfaces were inoculated with 1 to $5 \times 10^4$ colony forming units of bacteria by means of the Steers replicating device. The lowest concentration of antibiotic that inhibited growth of a bacterial strain after 18 hours incubation was recorded as the minimal inhibitory concentration (MIC) for that strain. The results are given in Table I.

Because of the lengthy nomenclature, the compounds in Table I have been coded as follows:

Compound I: Ammonolysis Product of LL-E19020 α and β.
Compound II: Methyl Ester of LL-E19020α.
Compound III: Methyl Ester of LL-E19020β.
Compound IV: Monosaccharide of Methyl Ester of LL-E19020α.
Compound V: Monosaccharide of Methyl Ester of LL-E19020β.
Compound VI: Aglycone Methyl Ester of LL-E19020β.
Compound VII: Triacetate Aglycone Methyl Ester of LL-E19020β.

TABLE I

In Vitro Antibacterial Activity of LL-E19020 α and β Derivatives

| Organism | | Minimal Inhibitory Concentration (mcg/ml) Compounds | | | | | |
|---|---|---|---|---|---|---|---|
| | | I | II | III | IV | V | VI |
| Streptococcus b-hemolyticus | C 203 | 8 | 0.12 | 2 | 4 | 8 | >128 |
| Streptococcus b-hemolyticus | VGH 84-60 | 4 | 0.5 | 2 | 2 | 8 | >128 |
| Streptococcus b-hemolyticus | VGH 0.5 | 16 | 2 | 8 | 8 | 32 | >128 |
| Streptococcus b-hemolyticus | VGH 84-62 | 16 | 2 | 8 | 8 | 32 | >128 |
| Streptococcus pneumoniae | SV-1 | 64 | 4 | 8 | 16 | 32 | >128 |
| Streptococcus pneumoniae | K 84-21 | >128 | 8 | 32 | 16 | 64 | >128 |
| Bacteroides vulgaris | ATCC 29327 | 128 | 128 | 16 | >128 | >128 | >128 |
| Clostridium perfringens | ATCC 13124 | >128 | 64 | >128 | >128 | >128 | >128 |
| Clostridium difficile | ATCC 17858 | 4 | 2 | 8 | 8 | 64 | >NT |
| Peptococcus magnus | ATCC 29328 | 0.25 | ≦0.06 | ≦0.06 | ≦0.06 | ≦0.06 | 0.5 |
| Peptococcus magnus | ATCC 14956 | ≦0.06 | ≦0.06 | ≦0.06 | ≦0.06 | ≦0.06 | 0.5 |
| Peptococcus asaccharolyticus | ATCC 29743 | 0.25 | ≦0.06 | ≦0.06 | ≦0.06 | ≦0.06 | 0.5 |

NT = Not tested

In therapeutic use, the compounds of this invention find utility in the suppression of bacterial infections and as general disinfectants for laboratories. As such they may be administered in the form of conventional pharmaceutical or veterinary compositions appropriate for the intended use. Such compositions may be formulated so as to be suitable for oral, parenteral, or topical administration. The active compounds may be combined in admixture with a pharmaceutically acceptable carrier, which carrier may take a wide variety of forms, depending on the form of preparation desired for administration, i.e., oral, parenteral or topical.

The invention will be described further by the following non-limiting examples.

EXAMPLE 1

Ammonolysis Product of LL-E19020α

A 9.69 g portion of LL-E19020α was dissolved in 250 ml of acetonitrile and 125 ml of ammonium hydroxide was added. After 14 hours, the mixture was diluted with 1 liter of water and acidified to pH 1 with 6N hydrochloric acid. The aqueous portion was separated and extracted with three 600 ml portions of ethyl acetate. The extracts were combined, washed with 200 ml of saturated sodium chloride solution, dried and then evaporated. The 9.0 g of residue was dissolved in 20 ml of methanol and injected onto a Waters Prep 500 column which had been equilibrated with 3 liters of 32% acetonitrile in 0.1N ammonium acetate pH 4.5. The column was eluted with the same solvent system at the rate of 100 ml per minute, collecting 300 ml fractions. After fraction 55, the eluting solvent was switched to 35% acetonitrile in 0.1N ammonium acetate pH 4.5 and elution continued for a total of 90 fractions. Fractions 70-79 were combined, extracted with ethyl acetate and the extract dried and concentrated. The 1.5 g of residue was purified by HPLC, eluting with 35% acetonitrile in 0.1M ammonium acetate pH 4.5 at a flow rate of 50 ml per minute. Fractions of 300 ml each were collected. Fractions 48-56 were combined and evaporated, giving 818 mg of the desired product.

EXAMPLE 2

Methyl Ester of LL-E19020α

A 20 g portion of LL-E19020α was dissolved in a mixture of 100 ml of dichloromethane and 100 ml of acetonitrile. A 75 ml portion of cold ethereal diazomethane was added. After 15 minutes, the entire reaction was chromatographed on silica gel, eluting with ethyl acetate. Fractions 1-6 were 250 ml each. Fractions 7-16 were 500 ml each. Fractions 5-11 were combined and evaporated, giving 12.5 g of the desired product.

EXAMPLE 3

Methyl Ester of LL-E19020β

A 30 g portion of LL-E19020β was slurried in 200 ml of ethyl acetate. Diazomethane was added in portions until the reaction was complete. The material was then filtered and evaporated. The residue was dissolved in 40 ml of ethyl acetate and purified by chromatography, eluting with 70% ethyl acetate in hexane, then after 15 liters the eluent was step-graded from 80% to 90% to 100% ethyl acetate. Fractions 27-54 were combined and evaporated, giving 12.0 g of the desired product.

EXAMPLE 4

Monosaccharide of the Methyl Ester of LL-E19020α

A 5.582 g portion of the methyl ester of LL-E19020α was dissolved in 75 ml of methanol and cooled to 0° C. A 15 ml portion of 5% hydrochloric acid in methanol was added and this mixture was stirred for 5 hours. The mixture was added to 200 ml of water and extracted with three 100 ml portions of ethyl acetate. The extracts were combined and lyophilized giving 4.97 g of solid. This solid was purified by chromatography eluting with the system buffered acid:acetronitrile (7:3). Fractions 67-70 were combined, concentrated, dissolved in t-butanol and lyophilized, giving 1.37 g of the desired product.

EXAMPLE 5

Monosaccharide of the Methyl Ester of LL-E-19020α

A 4.7 g portion of the methyl ester of LL-E19020α was dissolved in 50 ml of methanol and cooled to 0° C. A 25 ml portion of 3% hydrochloric acid in methanol was added and the reaction was stirred for 5 hours. The reaction was added to 100 ml of water and extracted with three 100 ml portions of ethyl acetate. The extracts were combined, washed with 25 ml of concentrated brine, dried and purified by chromatography, eluting with 50% acetonitrile/buffer. The appropriate fractions were combined and evaporated, giving 0.9 g of the desired product.

EXAMPLE 6

Aglycone of the Methyl Ester of LL-E19020β

A 20.6 g portion of the methyl ester of LL-E19020β was dissolved in 150 ml of methanol, cooled to about 0° C. and 50 of 5% hydrochloric acid in methanol was added. The reaction was stirred for 4 hours, then added to 500 ml of water and extracted with three 250 ml portions of ethyl acetate. The extracts were combined and lyophilized giving 18.06 g of crude product. A 1 g portion of this product was purified by reverse phase liquid chromatography, eluting 25 ml fractions with 50% acetonitrile in 0.05M ammonium acetate pH 4.5 at the rate of 10 ml per minute. Fractions 51-71 were combined and evaporated, giving 230 mg of the desired product.

EXAMPLE 7

Triacetate of the Aglycone Methyl Ester of LL-E19020β

A 200 mg portion of 4-dimethylaminopyridine was dissolved in 100 ml of dichloromethane with stirring. A 2 ml portion of acetic anhydride was added and after 5 minutes 1.5 g of the aglycone methyl ester of LL-E19020β was added with stirring. After 2 hours, 100 mg of 4-dimethylaminopyridine and 1 ml of acetic anhydride were added. After 4 hours, 150 mg of 4-dimethylaminopyridine and 1 ml of acetic anhydride were added. After stirring overnight the reaction was chromatographed on silica gel, eluting with hexane:- ethyl acetate (7:3). Fractions 13-19 were combined and evaporated, giving 1.34 g of the desired product.

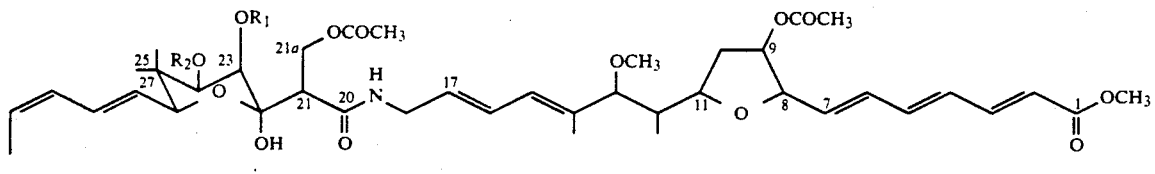

We claim:

1. The ammonolysis product of LL-E19020 α or β, having:

a) the structure

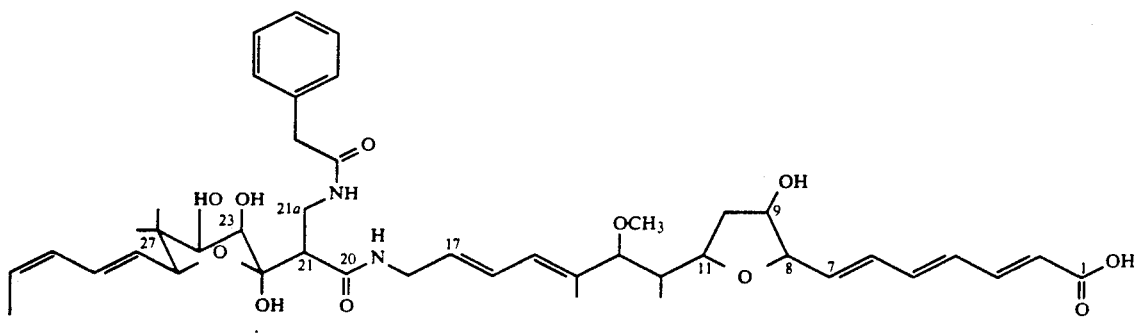

b) a characteristic ultraviolet absorption spectra as shown in FIG. I of the attached drawings;
c) a characteristic infrared absorption spectrum as shown in FIG. II of the attached drawings;
d) a proton nuclear magnetic resonance spectrum as shown in FIG. III of the attached drawings; and
e) a characteristic carbon-13-nuclear magnetic resonance spectrum as shown in FIG. IV of the attached drawings.

2. A compound selected from the (group consisting of the) methyl esters of LL-E19020α and LL-E19020β, having:
a) the structure

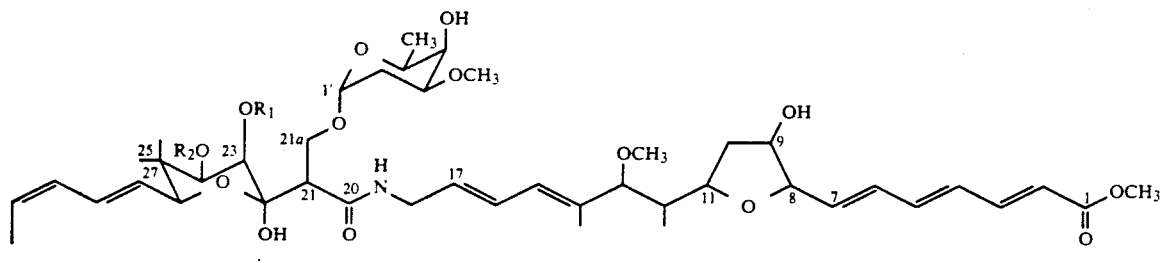

where, in the case of LL-E19020α, $R_1$ is benzylcarbonyl and $R_2$ is hydrogen and in the case of LL-E19020β, $R_1$ is hydrogen and $R_2$ is benzylcarbonyl, and LL-E19020β has a characteristic proton nuclear magnetic resonance spectrum as shown in FIG. V of the attached drawings.

3. A compound selected from the (group consisting of the) monosaccharides of the methyl esters of LL-E19020α and LL-E19020β, having:
a) the structure

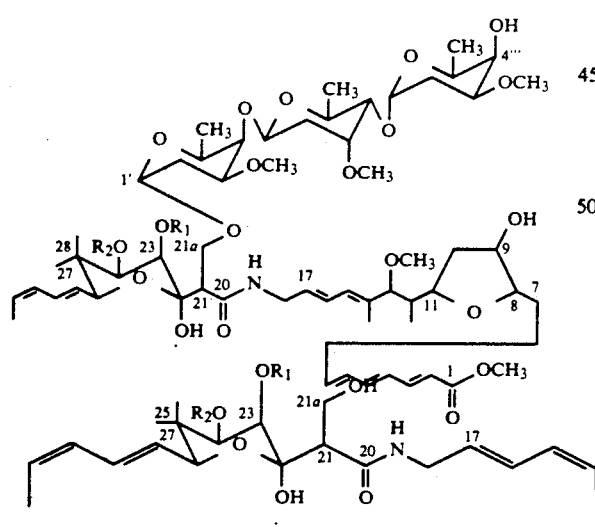

where, in the case of LL-E19020α, $R_1$ is benzylcarbonyl and $R_2$ is hydrogen and in the case of LL-E19020β, $R_1$ is hydrogen and $R_2$ is benzylcarbonyl, LL-E19020α having:

b) a characteristic infrared absorption spectrum as shown in FIG. VI of the attached drawings;
c) a characteristic proton nuclear magnetic resonance spectrum as shown in FIG. VII of the attached drawings; and
d) a characteristic carbon-13-nuclear magnetic resonance spectrum as shown in FIG. VIII of the attached drawings.

4. A compound selected from the (group consisting of the) aglycones of the methyl esters of LL-E19020α and LL-E19020β, having:
a) the structure

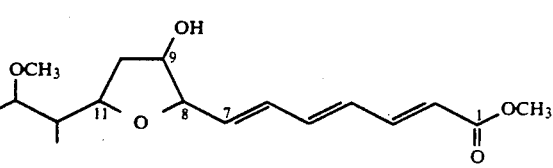

where, in the case of LL-E19020α, $R_1$ is benzylcarbonyl and $R_2$ is hydrogen, and in the case of LL-E19020β, $R_1$ is hydrogen and $R_2$ is benzylcarbonyl, LL-E19020α having:

b) a characteristic ultraviolet absorption spectra as shown in FIG. IX of the attached drawings;
c) a characteristic infrared absorption spectrum as shown in FIG. X of the attached drawings;
d) a characteristic proton nuclear magnetic resonance spectrum as shown in FIG. XI of the attached drawings; and
e) a characteristic carbon-13-nuclear magnetic resonance spectrum as shown in FIG. XII of the attached drawings;

and LL-E19020β having:
b) a characteristic ultraviolet absorption spectra as shown in FIG. XIII of the attached drawings;
c) a characteristic infrared absorption spectrum as shown in FIG. XIV of the attached drawings;
d) a characteristic proton nuclear magnetic resonance spectrum as shown in FIG. XV of the attached drawings; and
e) a characteristic carbon-13-nuclear magnetic resonance spectrum as shown in FIG. XVI of the attached drawings.

5. A compound selected from the (group consisting of the) triacetates of the aglycone methyl esters of LL-E19020α and LL-E19020β, having:
a) the structure where, in the case of LL-E19020α, $R_1$ is benzylcarbonyl and $R_2$ is acetyl and in the case of LL-E19020β, $R_1$ is acetyl and $R_2$ is benzylcarbonyl, LL-E19020α having:
b) an infrared absorption spectrum as shown in FIG. XVII of the attached drawings;
c) a proton nuclear magnetic resonance spectrum as shown in FIG. XVIII of the attached drawings; and
d) a carbon-13-nuclear magnetic resonance spectrum as shown in FIG. XIX of the attached drawings;

and LL-E19020β having:
b) a proton nuclear magnetic resonance spectrum as shown in FIG. XX of the attached drawings; and
c) a carbon-13-nuclear magnetic resonance spectrum as shown in FIG. XXI of the attached drawings.

6. A method of treating bacterial infections in warm-blooded animals which comprises administering to said animals an antibacterially effective amount of a compound selected from any one of claims 1, 2, 3, 4 or 5.

7. A pharmaceutical composition comprising an antibacterially effective amount of a compound selected from any one of claims 1, 2, 3, 4 or 5 in association with a pharmaceutically acceptable carrier.

* * * * *